US011896468B2

(12) United States Patent
Wang et al.

(10) Patent No.: US 11,896,468 B2
(45) Date of Patent: *Feb. 13, 2024

(54) DISPOSABLE ABSORBENT CORE AND DISPOSABLE ABSORBENT ASSEMBLY INCLUDING SAME, AND METHOD OF MAKING SAME

(71) Applicant: DSG TECHNOLOGY HOLDINGS LTD, Kwai Chung (HK)

(72) Inventors: Brandon Shui Ling Wang, Hong Kong (HK); Andrew C. Wright, Chesterfield (GB); Eugenio Varona, Marietta, GA (US)

(73) Assignee: DSG Technologies Holdings Ltd., Kwai Chung (HK)

( * ) Notice: Subject to any disclaimer, the term of this patent is extended or adjusted under 35 U.S.C. 154(b) by 944 days.

This patent is subject to a terminal disclaimer.

(21) Appl. No.: 16/660,199

(22) Filed: Oct. 22, 2019

(65) Prior Publication Data

US 2020/0113750 A1 Apr. 16, 2020

Related U.S. Application Data

(63) Continuation of application No. 15/055,249, filed on Feb. 26, 2016, now Pat. No. 10,524,966.

(Continued)

(51) Int. Cl.
*A61F 13/15* (2006.01)
*A61F 13/62* (2006.01)
(Continued)

(52) U.S. Cl.
CPC ........ *A61F 13/62* (2013.01); *A61F 13/15585* (2013.01); *A61F 13/15739* (2013.01);
(Continued)

(58) Field of Classification Search
CPC ............... A61F 13/62; A61F 13/15585; A61F 13/15739; A61F 13/49009; A61F 13/4906;
(Continued)

(56) References Cited

U.S. PATENT DOCUMENTS 4,525,229 A 6/1985 Suzuki et al.
5,147,487 A 9/1992 Nomura et al.
(Continued)

FOREIGN PATENT DOCUMENTS

EP 0623331 A2 11/1994
EP 0962207 A2 12/1999
(Continued)

OTHER PUBLICATIONS

Google Patents translation of Russian Patent No. RU2384314C2, Publication Date Mar. 20, 2010, [accessed translation on Jan. 22, 2020]. [10 pages].

(Continued)

*Primary Examiner* — Jacqueline F Stephens
(74) *Attorney, Agent, or Firm* — Alberto Q. Amatong, Jr.; Amatong McCoy LLC

(57) ABSTRACT

Disclosed is a disposable absorbent article having an outer shell and a detachable disposable absorbent core insert supported on an inside surface of the outer shell. The core insert is attached to the inside surface and is detachable therefrom. The inside surface further includes a retaining structure for receiving the absorbent core insert, the core insert being attachable with the retaining structure and detachable from the retaining structure.

31 Claims, 23 Drawing Sheets

Related U.S. Application Data

(60) Provisional application No. 62/121,399, filed on Feb. 26, 2015.

(51) Int. Cl.
*A61F 13/56* (2006.01)
*A61F 13/49* (2006.01)
*A61F 13/539* (2006.01)
*A61F 13/496* (2006.01)
*A61F 13/505* (2006.01)

(52) U.S. Cl.
CPC ........ *A61F 13/4906* (2013.01); *A61F 13/496* (2013.01); *A61F 13/49009* (2013.01); *A61F 13/505* (2013.01); *A61F 13/539* (2013.01); *A61F 13/565* (2013.01); *A61F 2013/5694* (2013.01)

(58) Field of Classification Search
CPC .... A61F 13/496; A61F 13/539; A61F 13/505; A61F 13/565; A61F 2013/5694
See application file for complete search history.

(56) References Cited

U.S. PATENT DOCUMENTS

| | | | |
|---|---|---|---|
| 5,300,058 | A | 4/1994 | Goulait et al. |
| 5,360,422 | A | 11/1994 | Brownlee et al. |
| 5,576,091 | A | 11/1996 | Zajaczkowski et al. |
| 5,613,959 | A | 3/1997 | Roessler et al. |
| 6,491,676 | B1 | 12/2002 | Suzuki et al. |
| 6,575,951 | B1 | 6/2003 | Ono et al. |
| 6,638,262 | B2 | 10/2003 | Suzuki et al. |
| 6,790,798 | B1 | 9/2004 | Suzuki et al. |
| 6,794,557 | B1 | 9/2004 | Klemp et al. |
| 7,166,095 | B1 | 1/2007 | Coates |
| 7,361,246 | B2 | 4/2008 | Chang et al. |
| 7,462,172 | B2 | 12/2008 | Wright et al. |
| 8,083,724 | B2 | 12/2011 | Bittner et al. |
| 8,157,781 | B2 | 4/2012 | Takino et al. |
| 8,568,380 | B2 | 10/2013 | Brownlee |
| 8,785,715 | B2 | 7/2014 | Wright et al. |
| 9,205,003 | B2 | 12/2015 | Tsang et al. |
| 10,524,966 | B2* | 1/2020 | Wang ............... A61F 13/15585 |
| 2002/0143316 | A1* | 10/2002 | Sherrod ........... A61F 13/53708 604/385.03 |
| 2003/0045855 | A1 | 3/2003 | Ono et al. |
| 2004/0158225 | A1 | 8/2004 | Coates |
| 2005/0137565 | A1 | 6/2005 | Bryant et al. |
| 2009/0320993 | A1 | 12/2009 | Yamamoto |
| 2010/0078119 | A1 | 4/2010 | Yamamoto |
| 2010/0179496 | A1* | 7/2010 | Roe .................. A61F 13/49004 604/397 |
| 2010/0179500 | A1 | 7/2010 | Roe et al. |
| 2011/0041999 | A1 | 2/2011 | Hundorf et al. |
| 2011/0130736 | A1 | 6/2011 | Tsang et al. |
| 2016/0278999 | A1 | 9/2016 | Wang et al. |

FOREIGN PATENT DOCUMENTS

| | | |
|---|---|---|
| JP | 2002000642 A | 1/2002 |
| JP | 2004538377 A | 12/2004 |
| JP | 2009125203 A | 6/2009 |
| JP | 2012515056 A | 7/2012 |
| JP | 2012200296 A | 10/2012 |
| JP | 2013146459 A | 8/2013 |
| RU | 2384314 C2 | 3/2010 |
| WO | 9403137 A1 | 2/1994 |
| WO | 9510992 A1 | 4/1995 |
| WO | 02080834 A2 | 10/2002 |
| WO | 2008014621 A1 | 2/2008 |
| WO | 2010083260 A1 | 7/2010 |
| WO | 2012009357 A1 | 1/2012 |
| WO | 2013095227 A1 | 6/2013 |
| WO | 2013097879 A1 | 7/2013 |

OTHER PUBLICATIONS

International Preliminary Report on Patentability issued in PCT Application No. PCT/US2016/019914, dated Sep. 8, 2017 [9 pages].
International Search Report dated May 5, 2016, during the prosecution of International Application No. PCT/US2016/019914. [3 pages].
Supplementary EP Search Report issued in EP Application No. 16756504.3 dated Jul. 20, 2018 [11 Pages].
Written Opinion dated May 5, 2016, during the prosecution of International Application No. PCT/US2016/019914. [7 pages].
Notice of Opposition to a European Patent filed by Essity Hygiene and Health Aktiebolag; filed in EP Patent No. EP3261598 on Jul. 10, 2020 (21 pages).

* cited by examiner

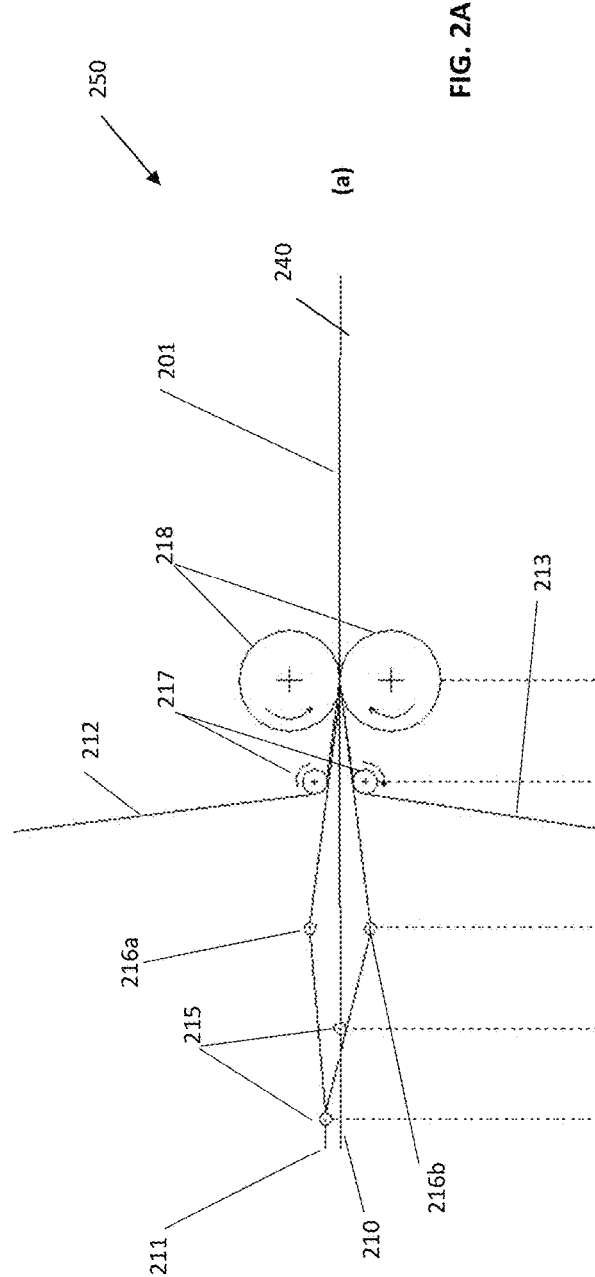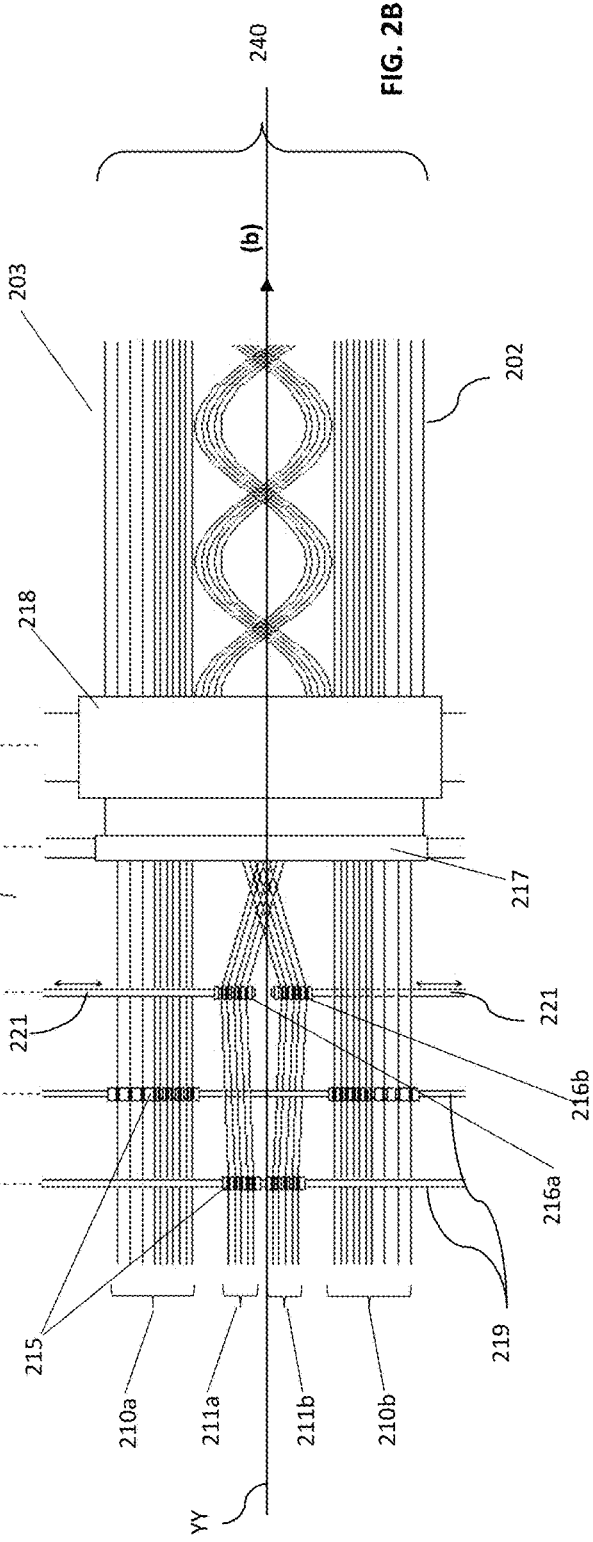

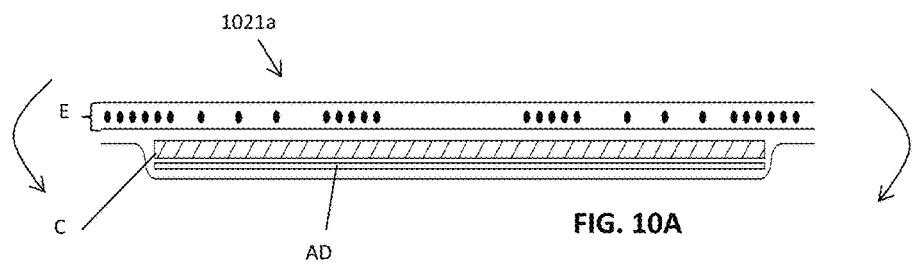
FIG. 10A
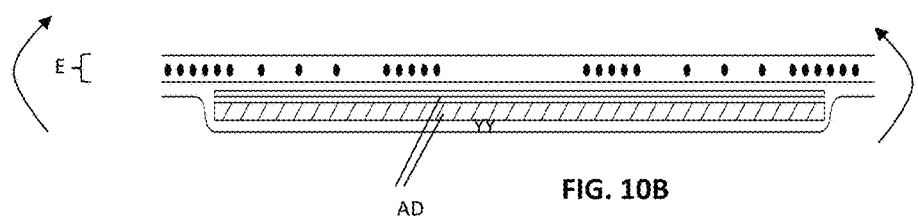
FIG. 10B
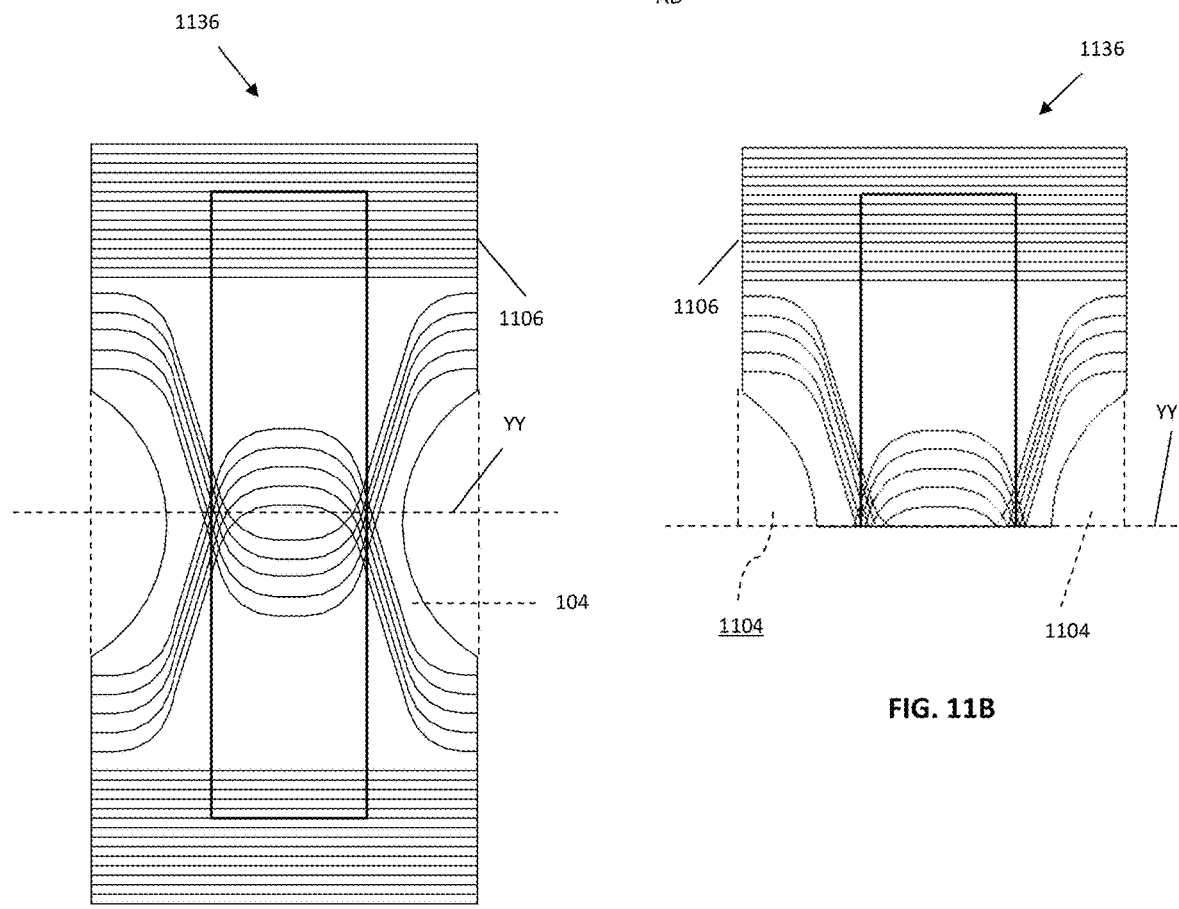
FIG. 11A
FIG. 11B

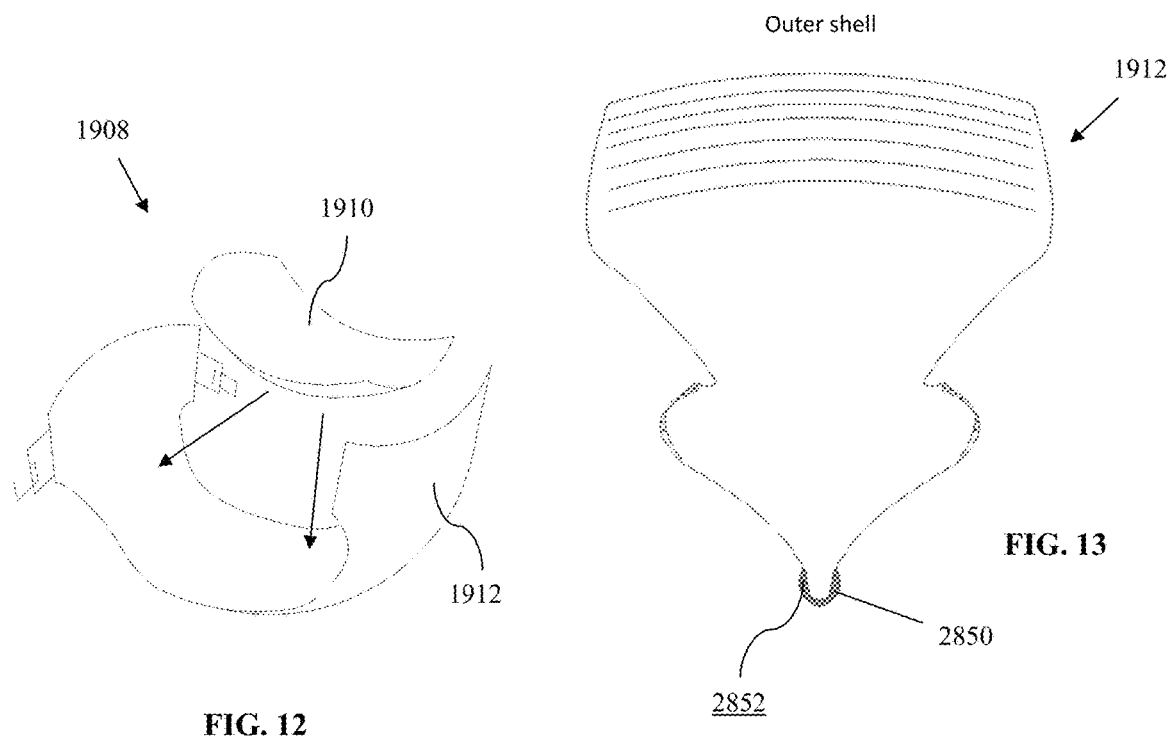
FIG. 12
FIG. 13
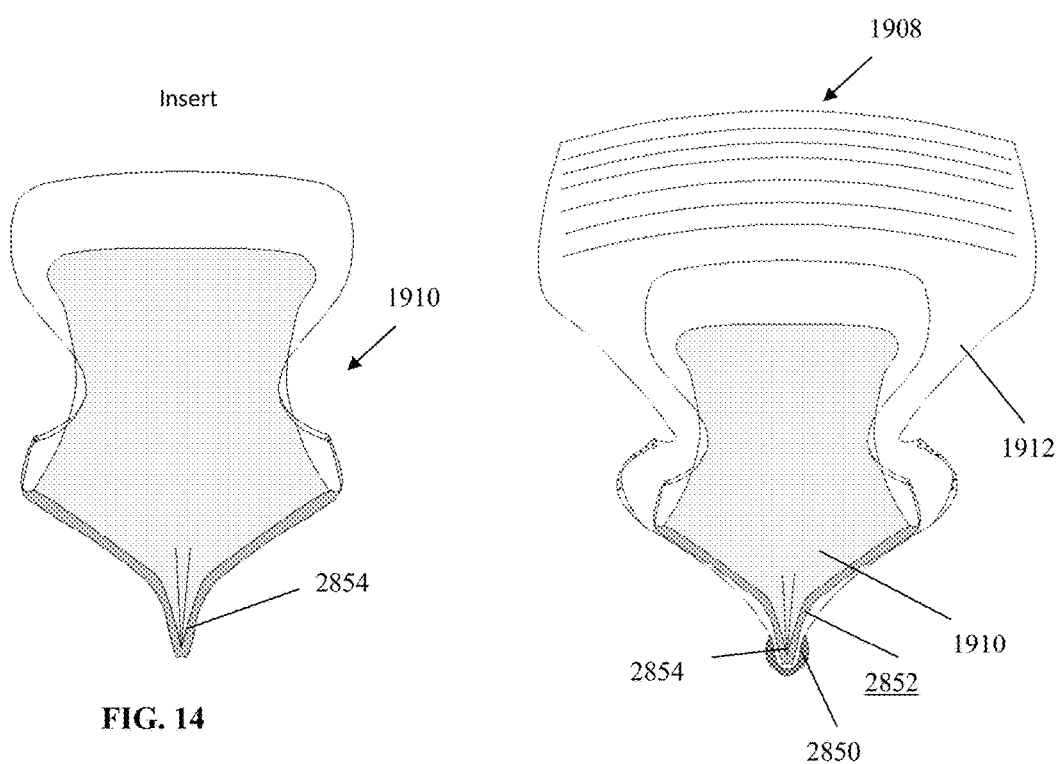
FIG. 14
FIG. 15

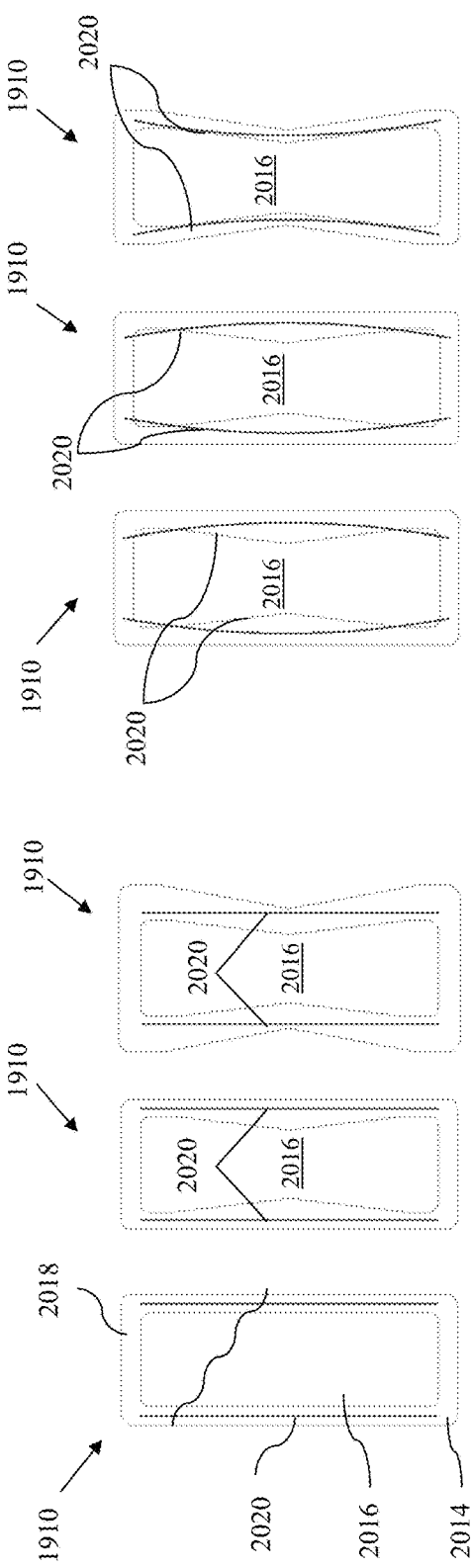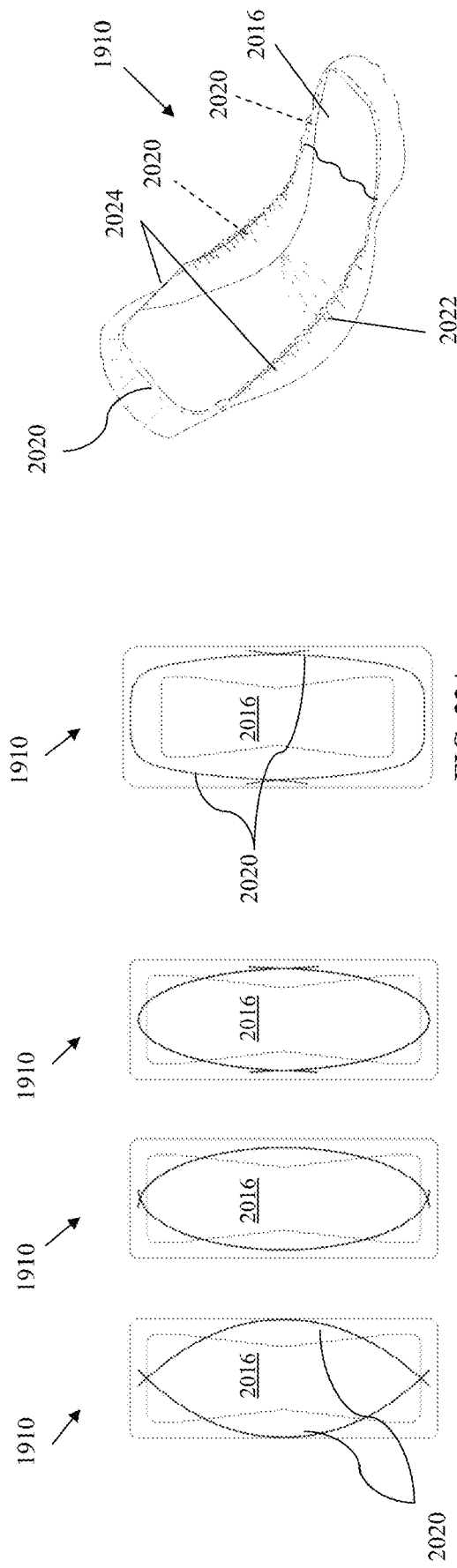

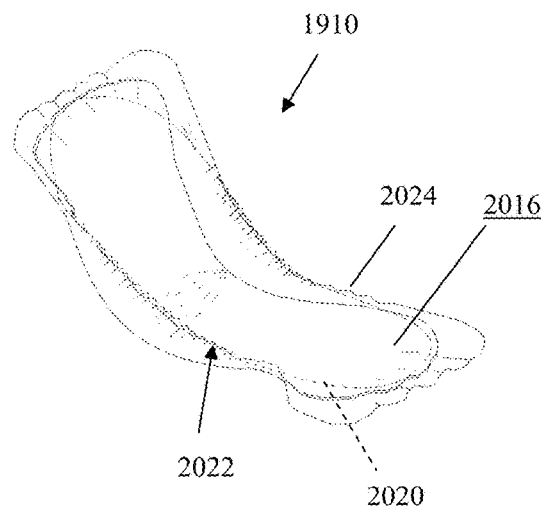
FIG. 24
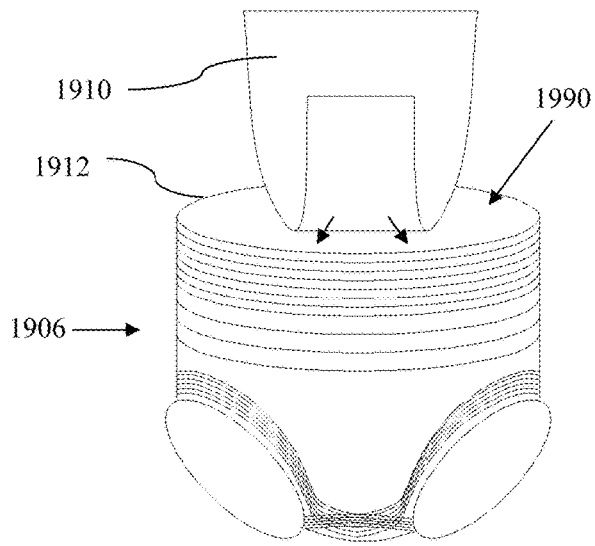
FIG. 25
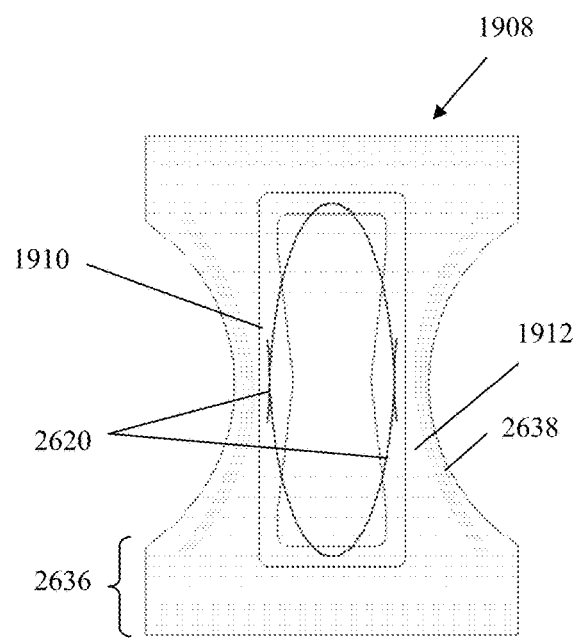
FIG. 26A           FIG. 26B

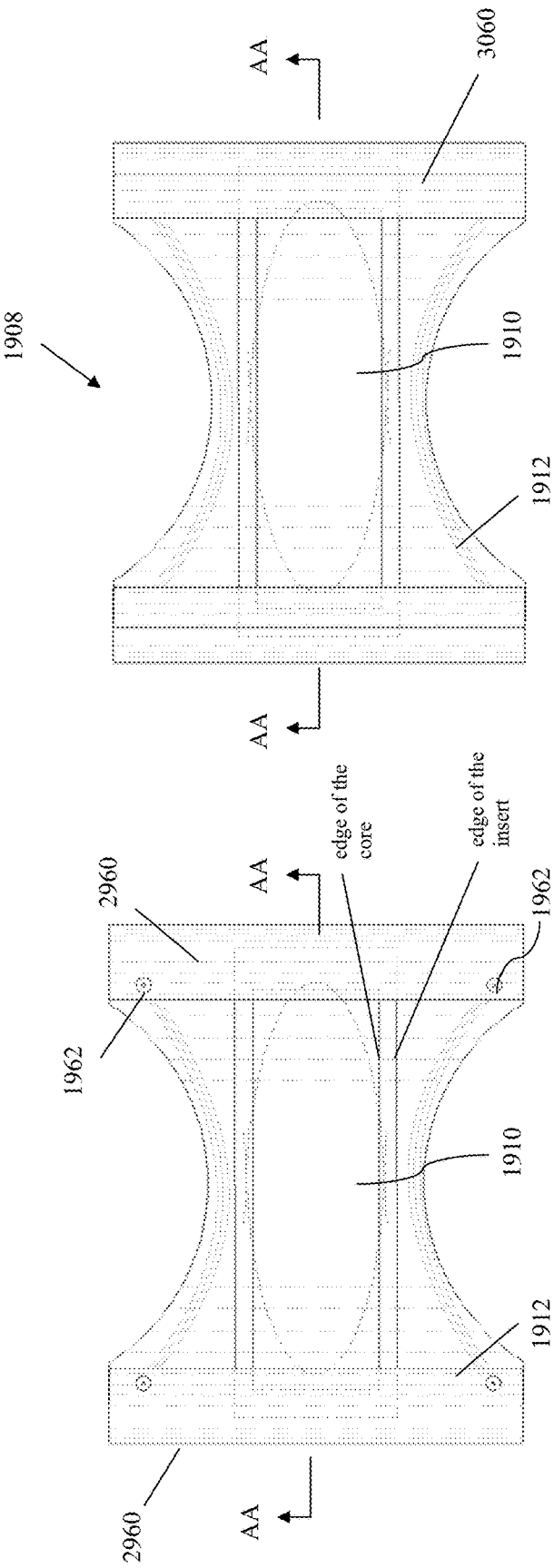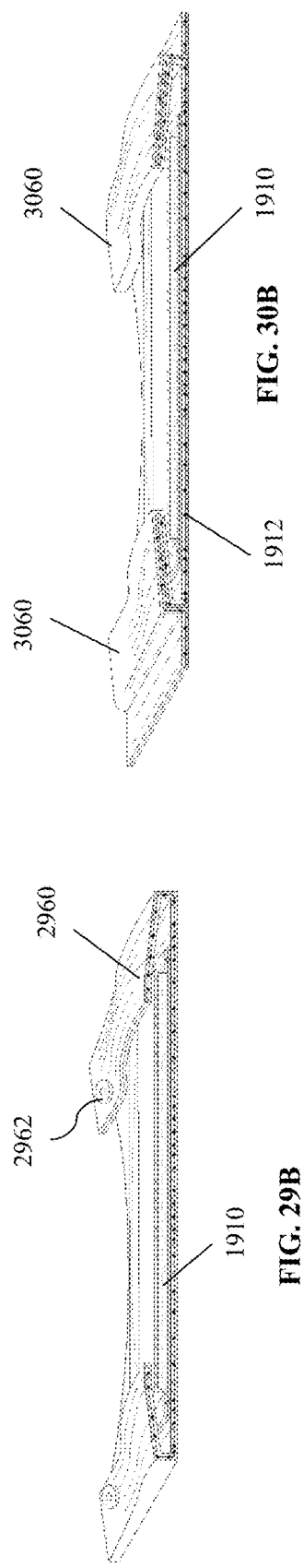
FIG. 30A
FIG. 30B
FIG. 29A
FIG. 29B

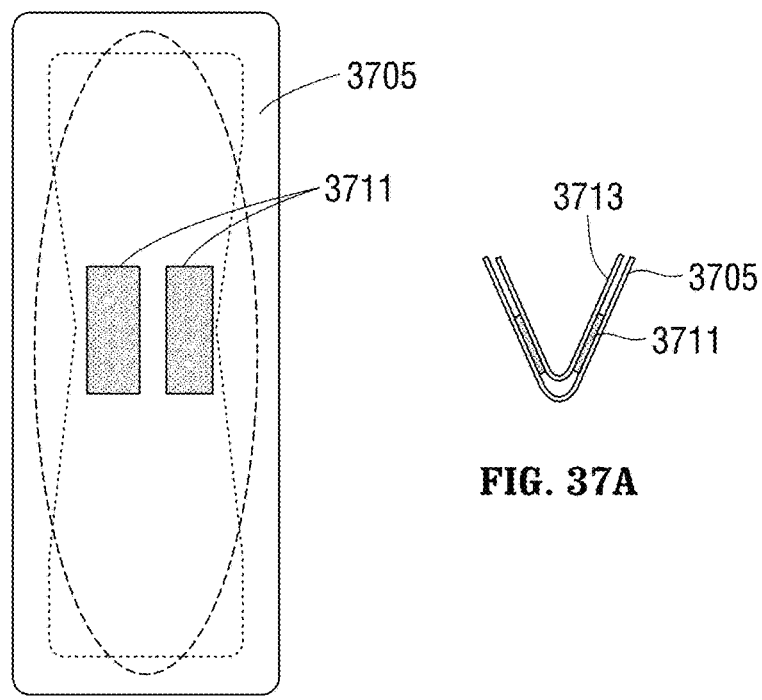
FIG. 37A
FIG. 37
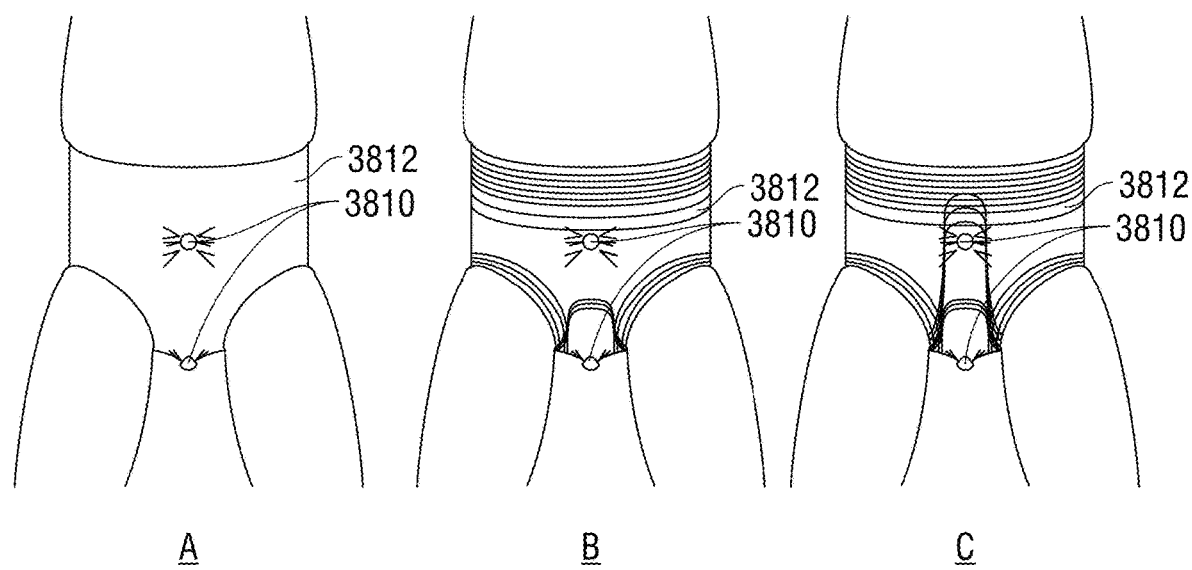
FIG. 38

DISPOSABLE ABSORBENT CORE AND DISPOSABLE ABSORBENT ASSEMBLY INCLUDING SAME, AND METHOD OF MAKING SAME

The present application is a Continuation application of U.S. application Ser. No. 15/055,249 filed on Feb. 26, 2016 (now allowed), which claims the benefit of the filing date of U.S. Provisional Application No. 62/121,399 filed on Feb. 26, 2015, which disclosure is hereby incorporated by reference for all purposes and made a part of the present disclosure.

BACKGROUND

The present disclosure relates generally to a disposable absorbent articles or garments, components therefor, and methods of making the same. More particularly, the present disclosure relates to an absorbent core of the article and further, the combination of a disposable absorbent core and a chassis or outer shell of the article, and methods of making the same.

Aspects of the present disclosure are particularly suited for, or related to, disposable absorbent articles such as baby diapers, training pants for infants and young children and adult incontinence diapers and pants. Specific embodiments may provide a web of elastic composite, an elastic composite or body, or elastic distribution patterns within these products, which, in turn, may improve the product's fit and comfort, its support and sealing capabilities, enhance the cost and manufacturability of the product and/or enhance the aesthetic qualities of the product.

Disposable absorbent articles contemplated herein include training pants, pull-on diapers, disposable underwear, and adult incontinence garments. As for training pants, these garments are used by young children to facilitate a child's transition from using diapers to wearing regular underpants (i.e., during toilet training). Training pants and other disposable pull-on pants have closed sides such that the user or caregiver raises the garment about the user's legs to wear the garment and slips the garment downward about the user's legs to take it off. These articles and garments are collectively referred to herein as "absorbent pants" or "pants products."

Elastic members may be incorporated into different parts of an absorbent garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of an absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of an absorbent garment, that part or area typically becomes a distinct, functional component of the garment. These elastic components include the side panels or ear portions, the waistband, and fastening tabs. Due in part to its multi-component construction, elastic composites may require a dedicated sub-process for manufacture which must be accommodated by the greater garment manufacturing process. Alternatively, the elastic composite may be manufactured independently or simply, manufactured in a separate sub-process detached from the central garment manufacturing system. In either case, a source of the elastic composite may be provided as input to the garment manufacturing process.

U.S. Pat. Nos. 7,462,172 and 7,361,246 and U.S. Pat. Appl. Publ. US 2012/0071852 provide background information on elastic composites (and the manufacture of such composites) of a type relevant to the present invention. Accordingly, these patent publications are also hereby incorporated by reference and made a part of the present disclosure, but only to the extent that incorporated subject matter provides background information and/or exemplary composites and processes suitable for use on, or with, the present inventive composites, systems, and methods. Thus, the incorporated subject matter shall not serve to limit the scope of the present invention. It should be noted that while these prior patent publications provide some discussion on making elastic composites and then incorporating same into absorbent articles, the present invention is, in one respect, more particularly directed to providing an improved system and method of making an elasticized absorbent article and/or a web of elastic composite bodies. More specifically, one directive of the present invention is to provide a method and system, whereby and wherein the elastic composite and its formation are seamlessly integrated into the method of making the article and into the elasticized article itself.

The products contemplated herein are disposable consumable goods intended to be purchased and packaged in volume. Moreover, the disposable absorbent goods are one-use products. Once used, the article is disposed and a new article takes it place. By their nature and because of the conditions under which the goods are used, a consumer can quickly go through and use a package of disposable absorbent articles. Thus, there is a desire, and perhaps, sometimes a product design objective to prolong the life of the product, and to minimize the number and cost of the articles that must be purchased. More generally, there is a desire to minimize the cost to the consumer to maintain a ready supply of disposable absorbent articles. The present disclosure relates to a product design directed to minimizing such cost, while also achieving certain performance objectives.

BRIEF SUMMARY

Disclosed is a disposable absorbent article having an outer shell and a detachable disposable absorbent core insert supported on an inside surface of the outer shell. The core insert is attached to the inside surface and is detachable therefrom. The inside surface further includes a retaining structure for receiving the absorbent core insert, the core insert being attachable with the retaining structure and detachable from the retaining structure.

In another aspect, a disposable absorbent core insert is disclosed for attaching to an outer shell of disposable absorbent article. The core insert includes a top material layer, a bottom material layer, and an absorbent core material layer disposed between said top and bottom material layers. A fastener is further included for attaching the core insert to an inside surface of a reusable outer shell of the absorbent article such that the core insert is detacheable therefrom. In some embodiments, the fastener includes a protruding portion on the bottom layer conformed to detachably engage a receptacle on the outer shell.

In another aspect, a disposable absorbent assembly is disclosed having an outer shell and a disposable absorbent core insert detachably engageable with the outer shell. The core insert includes an absorbent core material section having an absorbent composition. A method is also disclosed for making a disposable absorbent assembly, comprising providing a reusable outer shell and a disposable absorbent core insert, which entails detachably engaging the core insert within the outer shell, thereby assembling a disposable absorbent article for use, wherein the core insert provides a removable absorbent core of said absorbent article.

The foregoing has outlined rather broadly the features and technical advantages of the present disclosure in order that the detailed description that follows may be better understood. Additional features and advantages will be described hereinafter which form the subject of the claims of the invention. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the invention as set forth in the appended claims. The novel features which are believed to be characteristic of the products, systems, and methods, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

So that the manner in which the features and advantages of the system, products, and/or method so of the present disclosure may be understood in more detail, a more particular description briefly summarized above may be had by reference to the embodiments thereof which are illustrated in the appended drawings that form a part of this specification. It is to be noted, however, that the drawings illustrate only various exemplary embodiments and are therefore not to be considered limiting of the disclosed concepts as it may include other effective embodiments as well.

FIG. 2A is a simplified diagram in side view of a system or apparatus for making an elastic composite or elastic composite web;

FIG. 2B is a plan view of the system in FIG. 2A;

FIG. 10A is a cross-sectional view of a web of elastic composite bodies;

FIG. 10B is a cross-sectional view of an alternative web of elastic composite bodies;

FIGS. 11A-11B are simplified illustrations of an elastic composite body, according to yet another alternative embodiment;

FIG. 12 is a simplified perspective view of a disposable absorbent assembly including a detachable disposable absorbent core insert and a reusable outer shell;

FIG. 13 is a simplified vertical cross sectional view of an outer shell of a disposable absorbent article;

FIG. 14 is a simplified vertical cross sectional view of a disposable absorbent core insert shaped for receipt within the outer shell of FIG. 13;

FIG. 15 is a simplified vertical cross sectional view of a disposable absorbent article shown with the disposable absorbent core insert of FIG. 14 received and secured within the correspondingly shaped outer shell of FIG. 13;

FIGS. 16-18 are simplified plan views of a detached disposable absorbent core insert having straight-wise directed elastics applied thereon;

FIGS. 19-21 are simplified plan views of a detached disposable absorbent core insert having curved elastics applied thereon;

FIGS. 22A-22C are simplified plan views of a detached disposable absorbent core insert having circularly arranged elastics applied thereon;

FIG. 23A is a simplified plan view of a detached disposable absorbent core insert with a pair of circularly arranged elastics disposed about an absorbent core layer;

FIG. 23B is a perspective view of the detached disposable absorbent core insert of FIG. 24A;

FIG. 24 is a perspective view of the detached disposable absorbent core insert of FIG. 22C; and FIG. 25 is a front view of an outer shell of a disposable absorbent article receiving a disposable absorbent core insert;

FIG. 26A is a plan view of a disposable absorbent article incorporating a detachable disposable absorbent core insert, in a flat, laid-open configuration;

FIG. 26B is a plan view of an alternate disposable absorbent article incorporating a detachable disposable absorbent core insert, in a flat, laid-open configuration;

FIGS. 29A and 29B show a longitudinally directed cross sectional view of the disposable absorbent article of FIG. 28 along line AA-AA;

FIG. 30A is simplified plan view of an alternate disposable absorbent article equipped with an outer shell having folded end regions and a disposable absorbent core insert detachably retained therein;

FIG. 30B is a longitudinally directed cross sectional view of the disposable absorbent article of FIG. 30A along line AA-AA;

FIG. 35A is a cross-sectional view of a disposable absorbent article having the outer shell and core insert in FIG. 35;

FIG. 37 is a plan view showing an outer shell and core insert according to an alternative embodiment;

FIG. 37A is a cross-sectional view showing the outer shell and core insert of FIG. 35;

FIG. 38 are simplified illustrations, in front view, of disposable absorbent articles equipped with retainer clips, according to the present disclosure.

Figure 1A:
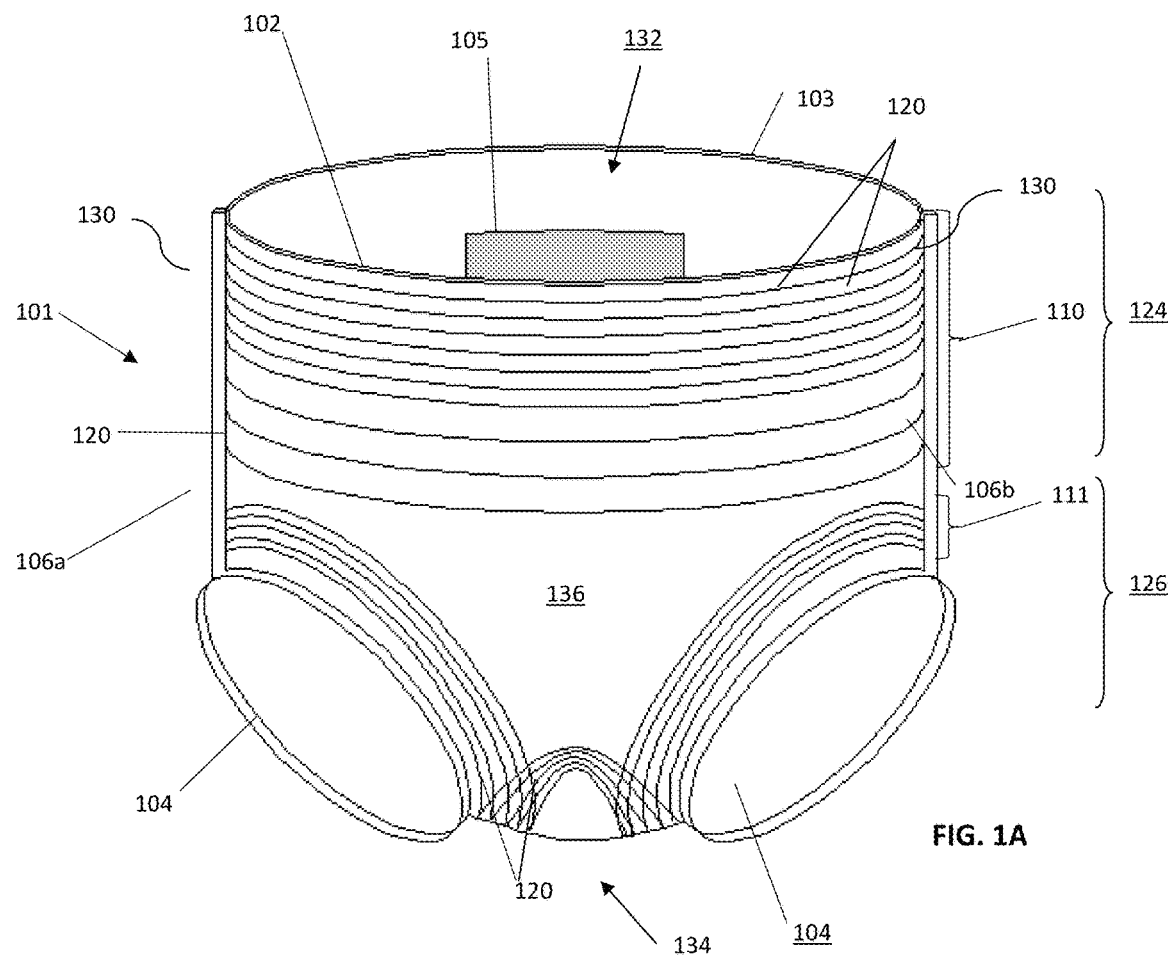
FIG. 1A is a simplified illustration in isometric view of a disposable absorbent article.

Products and methods according to present disclosure will now be described more fully with reference to the accompanying drawings, which illustrate various exemplary embodiments. Concepts according to the present disclosure may, however, be embodied in many different forms and should not be construed as being limited by the illustrated embodiments set forth herein. Rather, these embodiments are provided so that this disclosure will be thorough as well as complete and will fully convey the scope of the various concepts to those skilled in the art and the best and preferred modes of practice. For example, many of the exemplary descriptions provided herein are concerned with training pants for infants and young children or diapers. Aspects of the concepts described may, however, be equally applicable to designs for and the manufacture of adult incontinence products and other similar products.

DETAILED DESCRIPTION OF THE INVENTION

The present disclosure is directed, in one aspect, to a disposable absorbent core insert. The present disclosure is further directed to a combination of a disposable absorbent core insert and reusable outer shell with, or into, which the core insert is engaged or inserted. The disclosure is also directed to a disposable absorbent article or garment comprising the disposable absorbent core insert and reusable outer shell. In various or further applications, the disposable absorbent article or garment may take the form of a diaper, training pants, adult incontinence product, feminine hygiene product, and other similar disposable absorbent products.

FIGS. 1-11 provide descriptions of prior art systems and processes that serve as background for a detail description of the subject products and processes introduced herein. FIGS. 12-40B provide simplified illustrations of the absorbent products and components thereof, which are the subject of the present novel disclosure. The process techniques and product design illustrated FIGS. 1-11, and described in accompanying descriptions, may be employed in the design and production of the core insert and disposable absorbent products according to the present disclosure. For example, the process of establishing elastic distributions between material layers or producing elasticated bodies illustrated in one or more of FIGS. 1-11 may be adopted, partially or in full, in the design and manufacture of the new products.

Disposable Absorbent Article with Reusable Outer Shell and Disposable Absorbent Core Insert Now turning to FIG. 12 a particularly advantageous combination of a disposable absorbent core insert 1910 and a reusable outer shell 1912 is illustrated. In preferred embodiments, one or both the core insert 1910 and the outer shell 1912 originate as elastic composites that are elasticated by techniques described above. In certain applications, the outer shell provides a central body or chassis of an absorbent article or alternatively, represents the remaining and finished parts of the complete disposable absorbent article. In any case, the combination of the disposable core insert with the outer shell or with the remaining components of a disposable absorbent article may be referred to as a disposable absorbent article assembly 1908. As illustrated, the core insert 1910 is engageable with the outer shell 1912 to form a disposable absorbent garment or article such as a diaper 1908 (FIG. 12) or training pants\adult incontinence product 1906 (FIG. 25), or at least a central body or chassis therefor. The core insert 1910 is retained by and within the crotch region of the semi-enclosed garment 1906. The absorbent core insert according to the present disclosure is disposable and thrown away after each use. The outer shell 1912 is only semi-disposable, however, and may be used with up to 20-30 core insert replacements.

As used herein in respect to the engagement between the core insert and the outer shell, the terms "detachable" and "removable" both mean and refer to the core insert and\or the outer shell being configured and\or equipped (in contrast to a typical disposable absorbent article) to readily and repeatedly attach the core insert(s) to a predetermined location (i.e. a "landing") on the inside surface of the outer shell so as to provide an absorbent core of a disposable absorbent article (in crotch or target region). The terms further mean that the attachment is not permanent but temporary, and that the core insert may be removed without destruction or removal of components or the undoing of components, and such that the outer shell (and landing) may be used again to receive another "detachable" or "removable" core insert.

Background Systems and Processes

FIGS. 1-11 are particularly directed to designs and processes for disposable absorbent training pants, aspects of which may be adapted for use with embodiments of the present disclosure. The present disclosure and embodiments are applicable to disposable absorbent training pants but also adult diaper-pants and incontinence products, baby diapers, and other disposable absorbent wearable articles and garments, as well as components therefor and related methods of manufacturing. Certain of the elasticized chassis product design configurations illustrated in FIG. 1-11 may be suited or applicable for implementation in the design of the absorbent core insert and\or the outer shell illustrated in FIG. 12 and further described in this disclosure. See e.g., FIGS. 26, 27, and 38.

FIG. 1A illustrates a disposable absorbent training pants 101. The upright absorbent pants 101 is formed from an elasticized composite body 136 with a first or front half portion rotated about a symmetrical line to join a substantially identical second or rear half portion. The two half portions are joined at a pair of sealed side seams 130. Each side seam 130 consists of a first or bottom segment of a side edge 106 joined to a second or top segment of the same side edge 106 (as will be further explained below). The resultant absorbent pants 101 has a front longitudinal waist edge 102, a rear longitudinal waist edge 103, and the pair of sealed side seams or seals 130 each on a lateral side of the absorbent pants 101. The pants body 136 is sometimes described as having an upper waist region 124 and a lower waist, leg, and crotch region (lower region 126). The absorbent pants configuration 101 is also provided with a fluid distribution and storage construction or absorbent core 105 on the inside of the pants 101 and about a crotch region 134. In one aspect, the forming of the two lateral side seals 130 immediately creates the absorbent pants configuration 101. This absorbent pants configuration 101 includes a waist opening 132 defined by the joining of the two waist edges 103 to complete a continuously encircling waist edge. The pant configuration 101 further includes two leg openings 104 formed by the joining of the half portions (as will also be further explained below).

The pants configuration 101 also includes the lateral side seams 130. The side seams 130 may be provided by a permanently bonded seal or a refastenable seal. A permanent side seal may be achieved, for example, through the use of adhesive bonding, thermal bonding, ultrasonic bonding or any other suitable bonding mechanism. A refastenable side seal may be achieved through the use of adhesives, hook and loop materials or other refastenable mechanisms.

To enhance the comfort and fit of the absorbent article, as well as its capacity to contain fluid and minimize the occurrence of leakage of fluid through the waist and leg openings 132, 104, the disposable absorbent article 101 is provided with strategically-placed elastomeric materials 120. In a preferred embodiment, these elastomeric materials consist of strands or yarns of elastic thread such as natural rubber, latex strands or synthetic elastomers such as Lycra or Spandex yarns. Other suitable elastomeric materials include, but are not limited to, stretchable elastomeric films, elastomeric ribbons, elastomeric nonwovens and elastomeric adhesives. For purposes of this description, any discussion of the elastomeric materials will be confined to the use of elastomeric strands or yarns, which may be referred to as elastic strands or elastics. It will become apparent, however, that these elastomeric materials may be readily substituted with many other types of elastomeric material.

The absorbent pants 101 in FIG. 1 incorporate multiple distributions of elastic strands 120 in the upper waist region 124 and in the lower waist, leg and crotch regions (lower region 126). These distributions of elastic strands render the composite body 136 with strategically localized and advantageously configured elasticity. Upon sealing of the side edges 106, this feature translates directly and readily to the resultant absorbent pants 101 and ultimately, to the pants 101 as worn by the user. Accordingly, the pants 101 of the invention may be referred to as an elasticized disposable absorbent article 101. To elaborate, each of the elastic distributions in the absorbent pants 101 define a substantially annular area or region of elastics or elasticity. In the upper waist region 124, a set or distribution 110 of the elastic strands 120 is arranged generally circumferentially about the waist opening 132 and just below the joined waist edges 102, 103, and thus, encircles the waist of the user. Preferably, the elastic strands 120 are mutually spaced apart and generally parallel with the waist edges 102, 103. Accordingly, the absorbent pants 101 is equipped with a particularly advantageous annular region of elastic and elasticity snugly encircling the entire waist of the user and, acting therewith, to effectively seal the waist opening 132. In the lower region 126, multiple distributions of elastic strands 120 extend substantially completely about the leg openings 104 and the crotch region 134. One set or distribution 111 of elastic strands 120 encircle the leg opening 104 and forms an elasticized annular area or region thereabout. A third annular area or region of elastics is generally positioned centrally in the crotch region 134.

The elastic annular regions about the waist opening and the leg openings are advantageously maintained substantially all the way around the sealing subject (i.e., the potential opening between the waist and the waist edge 102,103 and the potential openings between the thigh and the circular side edge of the article 101). Moreover, the strength and direction of the elastic forces are maintained generally uniform about the openings. A more effective and more reliable seal is achieved because all potential leakage points around the opening are addressed. Uniformity in the elasticity about the waist or thigh also helps to prevent uneven fit, which can lead to a poor seal. Notably, the elastic distributions 110, 111 in the composite body 136 extend substantially all the way from one side edge to the opposite side edge (as explained below) and, upon formation of the pants configuration 101, extend substantially continuously (without ends) about the article 101. It should be understood, however, that the elastics of the annular regions do not necessarily have to touch or overlap. It is sufficient for the ends of elastics to be proximate to opposing ends so as to effect generally uniform elasticity about the sealing subject or edge, substantially similar to an actual ring of elastic placed thereabout.

It should be noted that the elastic strands 120 about the leg opening 104 may overlap into the crotch region 134. It should also be noted that the elastic strands 120 in the upper and lower regions 124, 126 are not necessarily mutually exclusive and elastic strands in one region may overlap and intersect elastic strands in the other region.

Figure 1B:
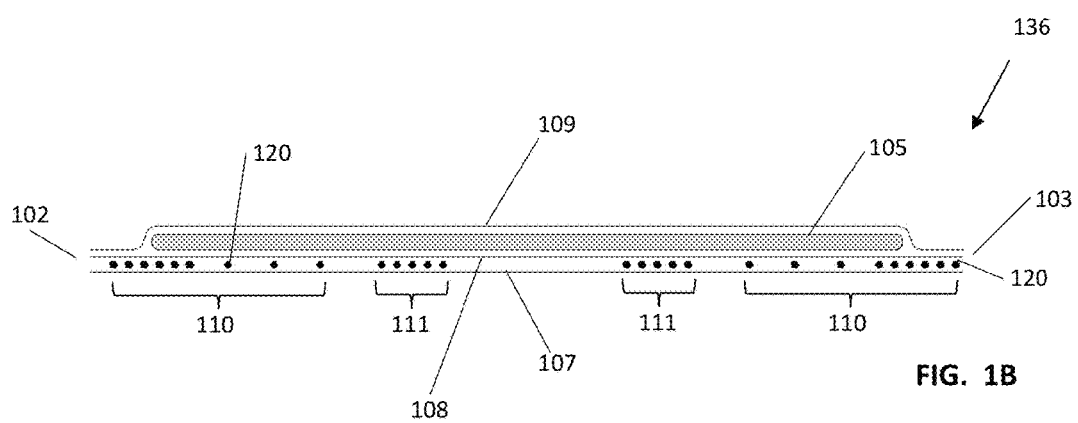
FIG. 1B is a cross-sectional view an elastic composite or elastic composite web.

The disposable absorbent article 101 having one or more annular regions of elastics or elasticity may be made utilizing a single, unitary elastic composite body 136 (or prior to making the pants configuration 101, simply elastic composite 136). FIG. 1B is a cross-sectional view of an exemplary elastic composite 136 specifically for the absorbent pants

101 of FIG. 1B. Among other things, this view describes the multiple distributions of the elastic strands 120 in the elastic composite 136 utilized in the absorbent pants 101. The elastic composite 136 has a first or bottom edge 102 and a second or top edge 103 (which ultimately define the waist edges 102, 103 in the pants configuration 101). The composite 136 also has an outer, fluid impermeable backsheet layer 107, an optional intermediate layer 108, a fluid distribution and storage construction or core 105 and a fluid permeable topsheet 109. The fluid impermeable backsheet layer 107 may be selected from a range of materials that include hydrophobic, fluid impermeable nonwoven materials, breathable and non-breathable polyethylene films or laminates of these materials. The optional intermediate sheet layer 108 may also include hydrophobic, fluid impermeable nonwoven materials, breathable and non-breathable polyethylene films, and laminates of said materials or other suitable materials. As shown in FIG. 1B, the two sheet layers 107, 108 help retain the elastic distributions 110, 111 in place, although, in some embodiments, the elastic distributions are adhered only to the surface of the backsheet layer 107. The fluid distribution and storage construction or absorbent core 105 may be composed of nonwoven materials, aperture films, tissue, cellulose fluff pulp, superabsorbent polymer particles or fibers or any other materials that can be utilized to distribute and absorb the fluid and solid insults passed into the article when it is used. Furthermore, fluid permeable topsheet 109 may comprise a hydrophilic, fluid permeable nonwoven web or an apertured material.

For the absorbent pants 101 of FIG. 1, the exemplary elastic composite 136 reveals a first distribution 110 of elastic strands 120 directed along each of the first edge 102 and the second edge 103. In this embodiment, a grouping of six spaced apart strands 120 is generally bunched together along the edges 102, 103, while three individual strands 120 are located inwardly of these strands 120. The spacing between the three individual strands 120 is wider than that of the first six strands 120. This spacing of strands 102, 103 corresponds with the spacing of the strands 120 in the upper region 124 of the disposable absorbent article 101 of FIG. 1A which concentrates elasticity near the edges 102, 103. The elastic composite 136 also features the two other distributions 111 of elastic strands 120. Two distributions 111 of five strands 120 each are located inwardly from the two outside distributions 110, as shown in FIG. 1B. As will be further described below, these two distributions 111 correspond with the elastic distributions 111 about leg openings 104 and in the crotch region 134 of the disposable absorbent article 101.

Figure 3:
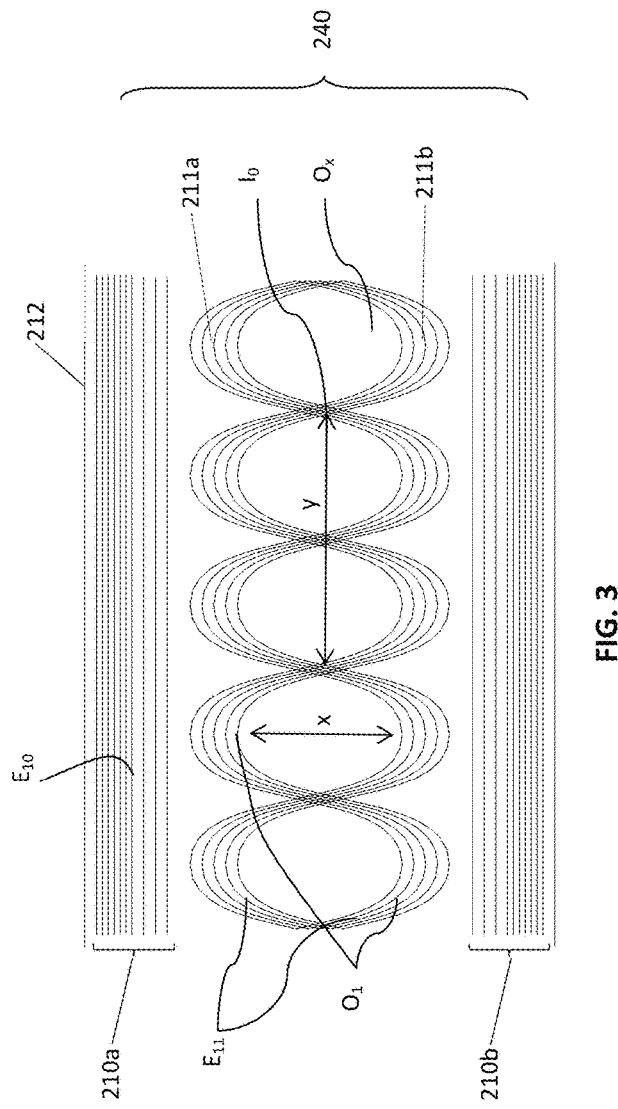
FIG. 3 is a simplified illustration of an elastic composite web.
Figure 4:
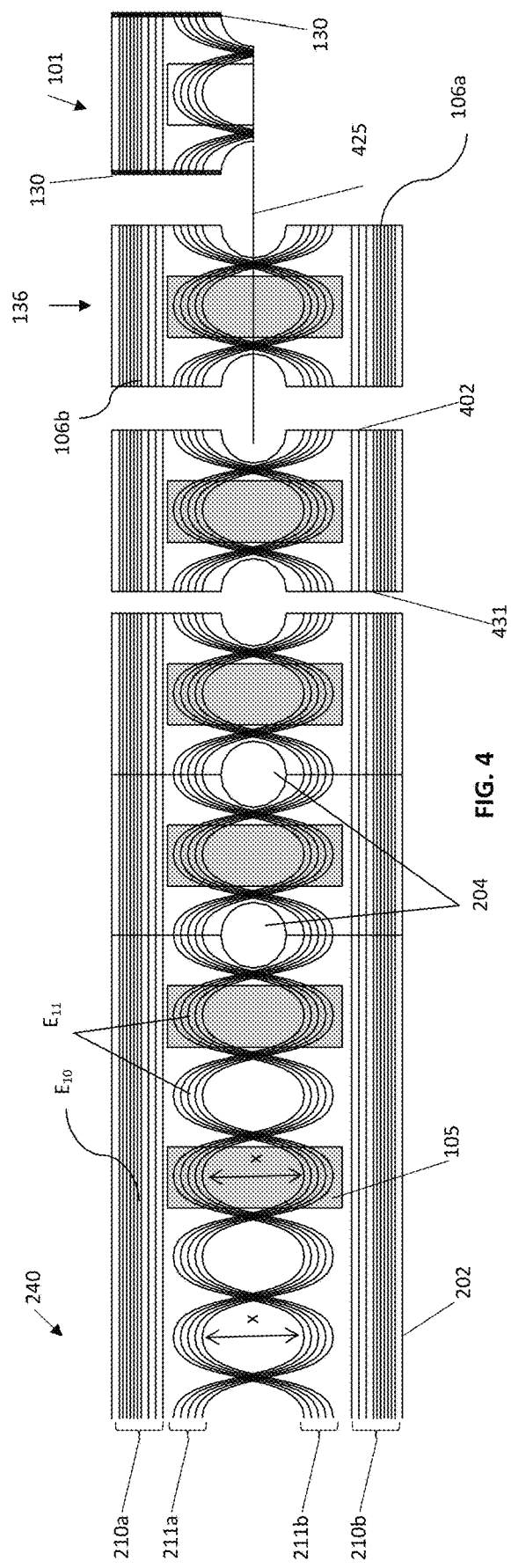
FIG. 4 is a simplified illustration of a web-based process for making the disposable absorbent article in FIG. 1.

The simplified illustrations of FIGS. 2A and 2B describe a system 150 and method for making a web 240 of the elastic composite 136. More specifically, the system 150 and method are utilized for incorporating the desired elastic distributions 110, 111 described above in an elastic composite 136 and in a composite web 240 (and ultimately, in an absorbent article 101), according to the invention. The illustrated method provides an initial sub-process in making the elastic composite 136 and the disposable absorbent article 101 in FIG. 1. FIG. 4 illustrates the subsequent and remaining stages in this method. Both FIGS. 3 and 4 depict a unitary elastic composite web 240 that is particularly suited for making disposable absorbent articles 101. As will be described, the composite web 240 can contain and present four continuous, machine-directioned distributions of elastic strands that trace a specific, advantageous pattern. At least two of the distributions are described by a periodic function featuring a trough and a summit. The other two distributions are preferably maintained along a direct path.

Referring now to FIGS. 2A and 2B, the system 250 and method convey, append, and manipulate an elastic composite web 240 in a substantially linear process and in the machine direction. For purposes of description, the web 240 is referred to as having a first or bottom edge 202, a second or top edge 203 spaced apart from the first edge 202 in the cross-machine direction and generally parallel therewith, a cross-machine width defined between the two edges 202, 203, and a longitudinal centerline YY. In some descriptions, the cross-machine direction across the web 240 and components supporting the inventive web 240 may be referred to as a lateral direction, while the machine direction may be described as corresponding to a longitudinal direction. Preferably, the elastic composite web 240 is advanced at a uniform rate of speed in the longitudinal or machine direction.

In a preferred embodiment, the method initially requires the separate, continuous conveyance of each of six elements of the elastic composite 136 to a joining mechanism such as a nip roller 218 (see e.g., FIG. 2A). These elements include a first material sheet 212, a second material sheet 213, a first set 210a of pre-tensioned elastic strands along the top edge 203, and a second set 210b of pre-tensioned elastic strands along the bottom edge 202. The first and second sets 210a, 210b of elastics strands are aligned in mutually parallel alignment but spaced apart specifically according to a predetermined arrangement. In this specific embodiment, the first and second sets 210a, 201b are mirror images of one another. Additionally, two other sets 211a, 211b of pre-tensioned elastic strands are conveyed along a machine direction laterally inwardly of the first and second sets 210a, 210b of pre-tensioned elastic strands. As best shown by FIG. 2A, both the first and second sets 210, 211 of elastics are preferably introduced and conveyed toward the nip roller 218 along the horizontal plane of the web 140. The two inwardly sets 211a, 211b of elastics are also introduced on the same web plane. The two material webs 212, 213, are on the other hand, preferably initiated from generally above and below the web plane, respectively (hence, sometimes referred to as upper and lower material webs or sheets).

The elastic strands may be received in a tensioned state by means of any suitable feeding and tensioning device positioned upstream of this process (not shown). The initial lateral positions of the elastic strands, as well as the spacing between adjacent elastic strands, are initially fixed by elastic guides 215. These fixed elastic guides 215 are mounted on two rods 219, as shown in FIGS. 2A and 2B. The elastic guides 215 typically comprise rollers, eyelets or any other suitable means for conveying and guiding the pre-tensioned elastic strands. A second set of elastic guides 216a, 216b are mounted on movable rods 221 downstream of the fixed rods 219. Each of these two movable elastic guides 216a, 216b engages one of the two inward sets 211a, 211b of elastic strands. Preferably, the movable rods 221 and movable guides 216a, 216b are positioned above and below the web plane, respectively. Thus, while a first set 211a of elastics is introduced along the web plane, it is directed slightly above the web plane a short distance after introduction. Similarly, the other set 211b is directed slightly below the web plane after introduction. This adjustment occurs before the two sets 211a, 211b of elastics are engaged by conveying means 217 and advanced to the nip roller 218.

It should be noted that the specific components of the system 250 shown in the Figures may be substituted with other suitable means or components. For example, in alternative systems, stationary guides or eyelets may be mounted on a fixed frame. Further, the movable guides may be mounted or associated with mechanical arms, cam systems, and other suitable mechanisms.

The sets 210a, 210b of elastic strands are distributed in a generally parallel alignment toward the nip roller 218. These elastic strands are analogous with the distribution 110 of elastic strands present in the upper waist region 124 of the absorbent article 101 in FIG. 1 and are distributed in parallel relationship with the top and bottom edges 202, 203 composite web 240. For the absorbent pants 101 of FIG. 1, the arrangement of the sets 210a, 210b of elastic strands must be identical. Other article designs may be provided, however, wherein the arrangements are not identical and one set may include more elastic strands than the other set. Also, the spacing and concentration of the elastics may, in other designs, differ to achieve a specific function or aesthetic attribute. Although such designs may deviate from the preferred arrangements for annular elastic regions, as described above, it is expected that such alternate designs will not deviate completely and that some aspects of the preferred designs will be retained (in accordance with the invention).

The moveable elastic guides 216a 216b are configured to move in a direction orthogonal to the machine direction of the web 240 and serve to change and direct the placement of the sets 211a, 211b of elastic strands into the nip roller 218 and adjust the lateral spacing of the elastic strands. Accordingly, the two inward sets 211a, 211b of elastics may be referred to as variable (as opposed to "fixed") sets of elastics. By vertically spacing the two variable sets 211a, 211b of elastics (as described above), the two sets 211a, 211b can move laterally without interference from the other. In this embodiment, for example, the two sets 211a, 211b of elastics laterally cross so that a bottom set of elastics arrives at the nip roller 218 as the top side set while the other set becomes the bottom side set.

Preferably, the elastic guides 216a and 216b are mounted on a reciprocating mechanism such that the elastic guides are continually reciprocating in a lateral direction (orthogonal or transverse to the machine direction of the process). The guides 216a, 216b may be carried on the same continuous belt or track and move together at all times. In other embodiments, the guides 216a, 216b may be driven independently of one another, particularly if the pattern of on elastic distribution is greatly independent of the other. Suitable driving mechanisms can include a cam based mechanism, a servo driven mechanism or a hydraulic mechanism. Preferably, the motion of the elastic guides 216a and 216b is described by a periodic function, in which a relative displacement of the elastic (or elastic guide) is a function of time (or a length of the web) plus a discrete increment (P, period). This displacement function expresses the periodic shape or pattern of the distributed elastics.

Figure 2C:
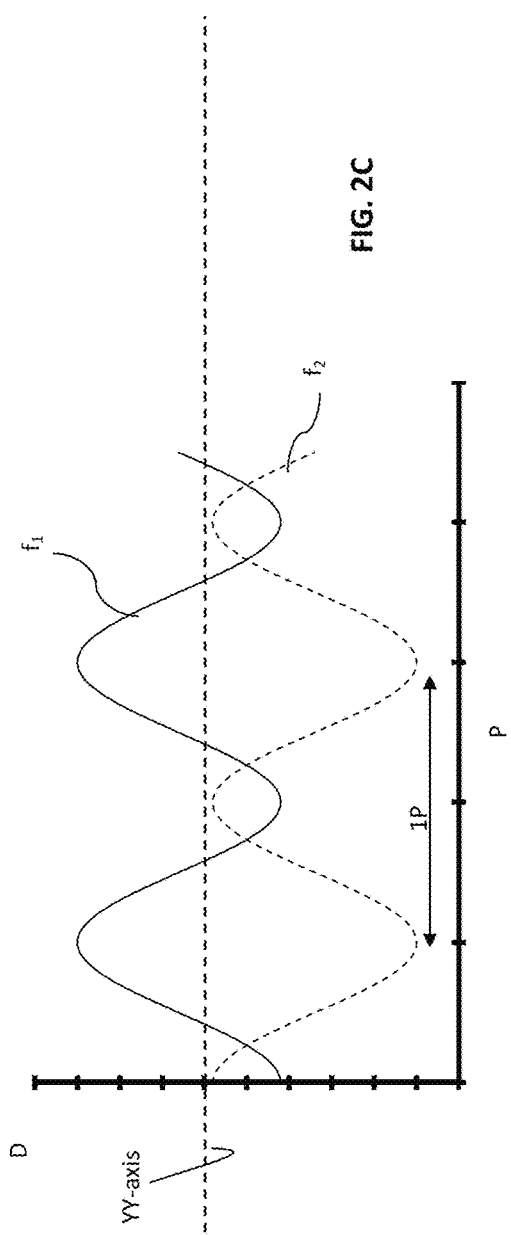
FIG. 2C is a graphical diagram of an exemplary periodic function reflecting directive lateral motion by elastic guides in FIGS. 2A-2B to produce a dual elastic distribution pattern on an elastic composite web.

The graphical illustration of FIG. 2C describes an exemplary periodic function reflecting the lateral displacement (D) of the movable guides 216a, 216b over a period of time (P) (which is proportional to the width of the elastic composite 136 relative to machine speed). The two separate functions f1, f2 show the relative lateral movement of the guides required to produce the dual elastic distribution patterns on the web. As shown by the graph, the two elastic guides necessarily cross twice during each period. The multiple crossings translate to the generation of a series of elastic annular regions on the composite web, or at least two annular regions per period (P) or elastic composite body 136.

The upper and lower sheets 212, 213 are also directed by conveyance means 217 toward the web plane and then to nip roller 218. Thus, the two sheets 212, 213 and the four sets 210, 211 of elastics arrive substantially together at the nip roller 218. The upper and lower sheets 212, 213 served to sandwich, entrap and hold the elastic strands in position after passing through the nip roller 218. The resultant web 240 of elastic material and material webs is secured using any suitable bonding means which include, adhesive, ultrasonic or thermal bonding (not shown). In the case of adhesive bonding, the adhesive could be applied to the upper and lower sheets 212, 213 or applied directly to the sets 210, 211 of elastic strands at any point prior to the elastic strands and upper and lower sheets meeting and combining at the nip roller 218.

FIG. 3 illustrates the continuation of the system 250 and method of making the disposable absorbent article 101 illustrated by FIGS. 2A, 2B. The system 250 and method of FIGS. 2A and 2B output an elastic composite web 240 that includes an upper sheet 212, a lower sheet not shown, but directly underlying the upper sheet 212, and distributions E10, E11 of elastic strands across the cross-machine direction width of the web 240. The two variable distributions E11 of elastic strands disposed in the middle are directed by means of the periodic, lateral motion of the elastic guides 216a, 216b in FIG. 2 (and its periodic function), which in this example, result in a sinusoidal pattern. The pattern may also be described as a series of annular elastic regions O1 or areas formed by the troughs and valleys of the two variable distributions E11 of elastics. Other linear and non-sinusoidal patterns may be produced by this process; but, for the purposes of this exemplary description, the sinusoidal pattern is employed. One set 211a of elastics is distributed in a first sinusoidal pattern E11 and are overlapped with the elastics of the second set 211b which are distributed in a second sinusoidal pattern E11. In this example, the first and second sinusoidal patterns are mirror images of each other. The two distributions E11 also define a region 1x at which one set overlaps and intersects the other. The degree to which the elastic strand patterns overlap can be measured and is, hereafter, described as the variable "X". The wavelength of the sinusoidal pattern can also be measured and is hereafter recorded as the variable "Y". Both variables "X" and "Y" are process parameters that may be adjusted by changing various process parameters such as machine speed, reciprocation speed and reciprocation depth.

FIG. 4 illustrates a process or conversion step for further modifying and then converting the elastic composite web 240 of FIGS. 2 and 3 into the disposable absorbent article 101 in FIG. 1A. As shown in FIG. 4, the sub-process proceeds downstream from left to right whereby the initial step may be described as receiving an output (the elastic composite web 240) from the system 250 and sub-process of FIGS. 2A and 2B. A fluid distribution and storage construction or core 105 is applied centrally over one of the overlap regions Ox of the two sets 211a, 211b of sinusoidal elastic strands. The elongated core 205 is applied and positioned laterally with the length of the core 205 being deposited on the web 240 in the cross-machine direction. In this embodiment, the core 205 is situated between the upper and lower distributions E11 of elastics. Simultaneous with or immediately after the application of the core 205, a material sheet 209 (not shown) is applied over the core 205 and the web 240. This material sheet becomes the topsheet in the disposable absorbent article 101. Additional features such as free-standing elasticised leg cuffs, fastening tapes and disposal tapes may be added to the construction at this stage.

In a subsequent step or stage in the process, preferably circular holes 204 are punched or cut in the web 240. In this embodiment, the holes 204 are punched centrally inside of the elastic annular regions O1, but on the overlap region Ox. As shown in FIG. 4, the holes 204 are also in longitudinal alignment with the intersections 1x of the elastic strands and with the wavelength distance "Y" of the sinusoidal patterns. The cutting of the holes 204 leads to the provision of the leg openings 104 in the disposable absorbent article 101. It is, therefore, an important requirement of the disposable absorbent article 101 that the wavelength "Y" of the sinusoidal pattern is equal to the width of the finished article 101.

The next step in the production process entails cutting or severing the continuous composite web 240 across the cross-machine direction width and along cutting lines 431. This end cut can be accomplished by a number of mechanisms known to those skilled in the art, including a die cutting process or a water-jet cutting process. The position of the end cut is determined relative to the wavelength "Y" of the sinusoidal pattern. Notably, cutting lines 431 bisect each hole 204 and alternating elastic annular regions O1. The cutting lines 431 are also spaced on either side of the core 205.

Upon separation, discrete, individual elastic composites 136 are formed. The elastic composite 136 now has a longitudinal (lengthwise) centerline that bisects the elongated core 105. Further, the composite 136 has two lateral side edges 106a, 106b along the original cutting lines. The side edges 106a, 106b consists of a top segment and a bottom linear segment. The non-linear cut-out section is positioned intermediate the two segments and is intended to form the leg openings. The elastic composite 136 also feature half elastic annular regions extending to each side edge 106a, 106b, which were severed by the cutting lines, and complete annular elastic annular regions in the center. The elastic composite 136 also has a core 105 situated centrally over the central elastic annular region.

Finally, the elastic composite 136 is folded along fold line 425 which corresponds to the longitudinal axis YY of the web 140. The elastic composite 136 in this embodiment is symmetric about this axis YY. Accordingly, when folded, each feature or portion on the bottom half match and cover the exact same feature or portion on the top half. The result is the disposable absorbent article 101 in FIG. 4 (and FIG. 1A). In the flat and folded state, the article 101 now displays a quarter of each leg 104 hole and a quarter of each half-annular region on the side edges 106a, 106b. To finalize the absorbent pants construction, the matching side edges 106a, 106b are sealed (seals 130), while the matching upper-lower edges 102, 103 and the quarter-leg holes are not. The specific manufacturing process for this embodiment employed a high "X" value.

The process described with reference to FIGS. 2-4 is one example of the process of making the inventive absorbent article. It is not required that the steps described are completed in the order described. It is possible, and may in some circumstances be preferred, that the steps are completed in a different order or that some of the steps may be completed simultaneously Now turning to the alternative illustration and schematic of FIG. 6, an alternative system 650 and method of making the disposable absorbent article utilizes a few different steps and sequences. A first material sheet 612 is conveyed separately by conventional means. Pre-tensioned elastics 610 (for the upper waist regions) are applied on the sheet 612, preferably near the side edges, as previously described. The resulting elastic composite 640 is then conveyed toward and by conveying means 617. Two sets 611a, 611b of elastics are also moved and conveyed toward the conveying means 617, utilizing elastic guides 616a, 616b. As before, the elastic guides 616a, 616b vary the lateral position of the set 211a, 211b of elastics in accordance with a periodic function and to elicit a preferred pattern. Thus, the elastic composite web 640 meets the two sets 611a, 611b of variable elastics at nip roller 618, thereby enhancing the original web 640 with preferred distributions of elastics. These preferred distributions include a series of annular regions, as in earlier-described embodiments.

Figure 6:
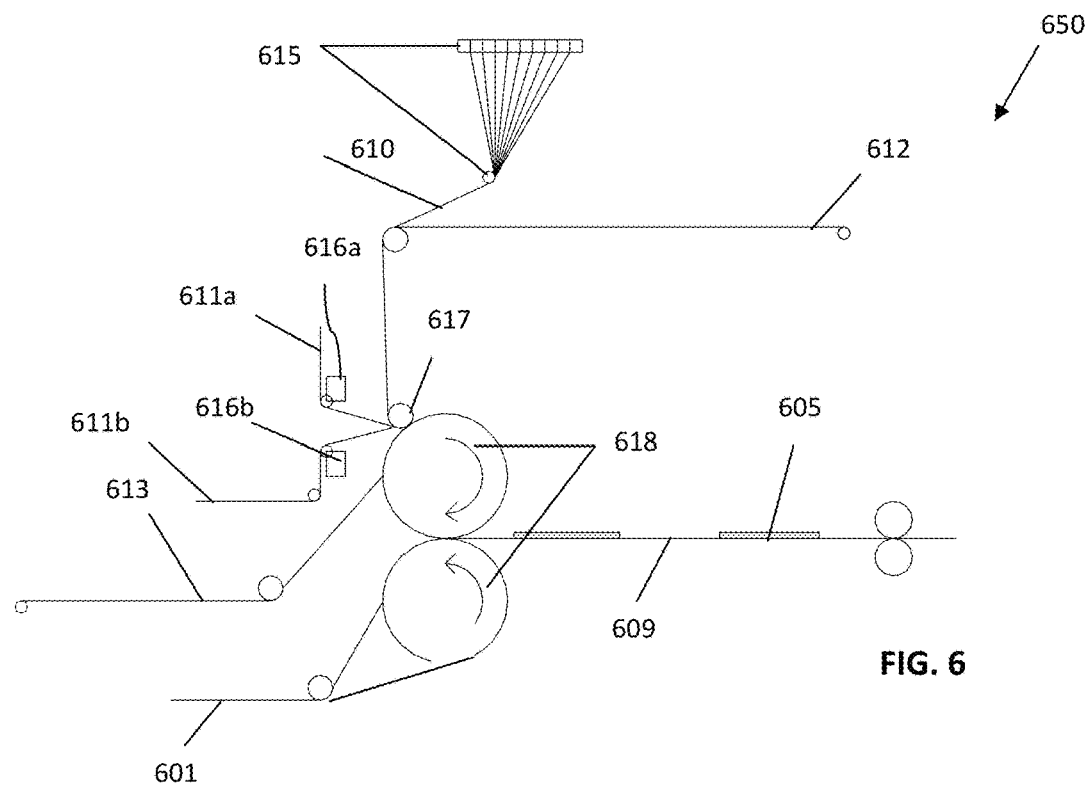
FIG. 6 is a simplified schematic of system for making the disposable absorbent article in FIG. 1.
Figure 7A:
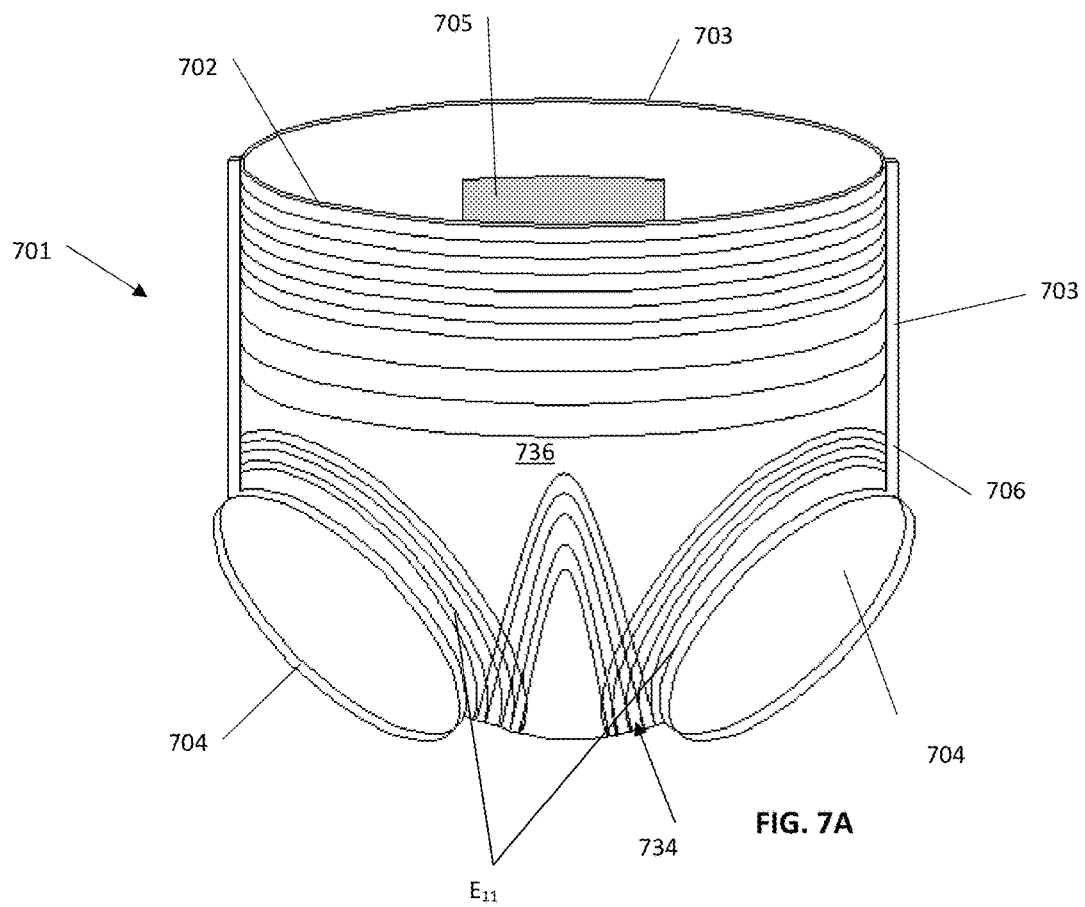
FIG. 7A is a simplified illustration in isometric view of a disposable absorbent article according to an alternative embodiment.

Furthermore, a separate combination web 609 is applied on the elastic composite web 640 by a second nip roller 618. This subsequent application includes incorporation of a web of sheet material upon which core materials are already intermittently deposited, as shown in FIG. 6. The resulting output of the second nip roller 618 is an elastic composite web 640 having two material sheets and two sets of variable elastics and two sets of mutually parallel pre-tensioned elastics, similar to the outputs of the systems and processes of FIGS. 2A, 2B.

Figure 7:
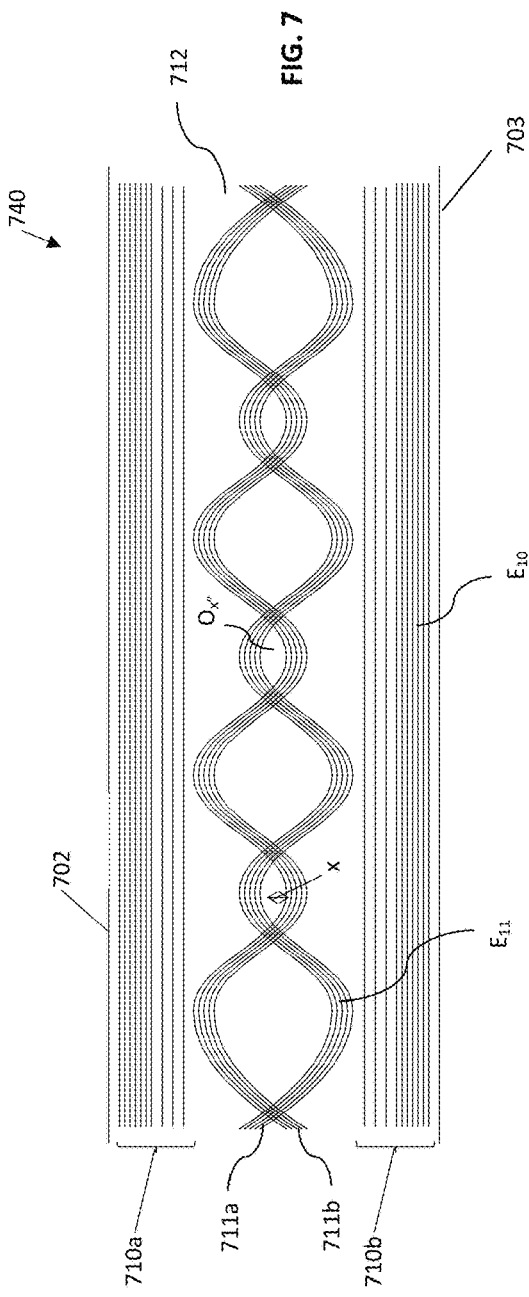
FIG. 7 is a simplified illustration of an elastic composite web employed in a web-based process for making a disposable absorbent article.
Figure 5:
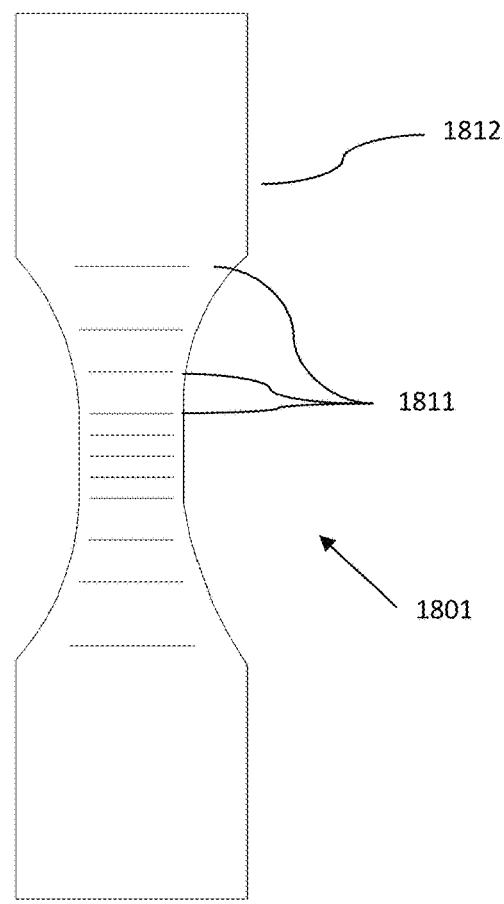
FIG. 5 is a simplified illustration of an elasticized core structure achievable by the system and process.
Figure 8:
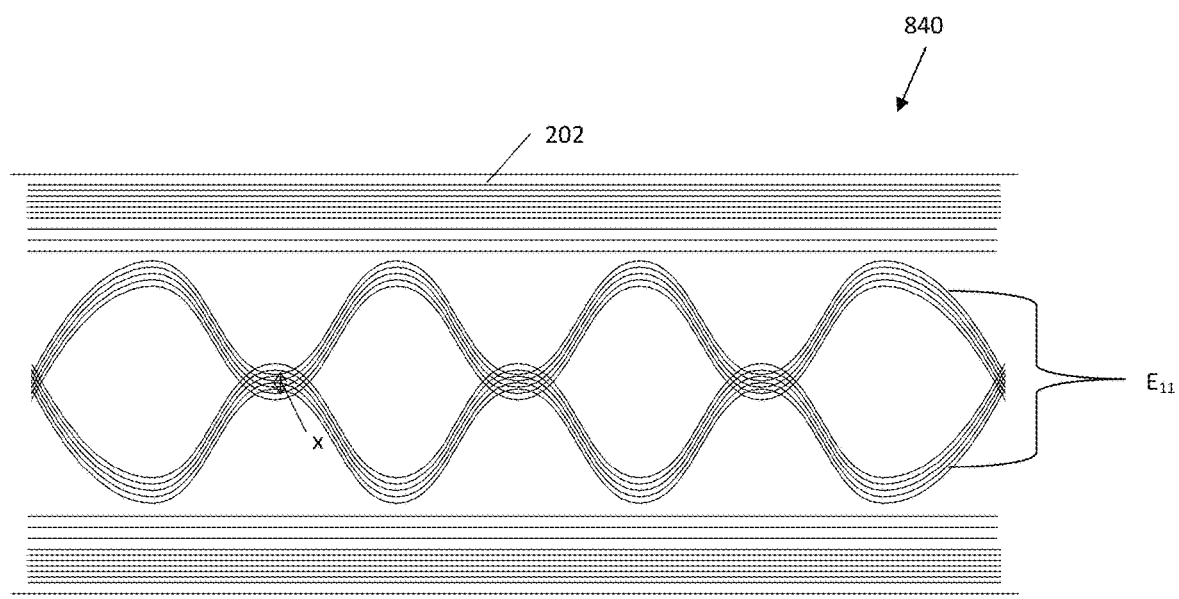
FIG. 8 is a simplified illustration of yet another alternative elastic composite web.
Figure 9:
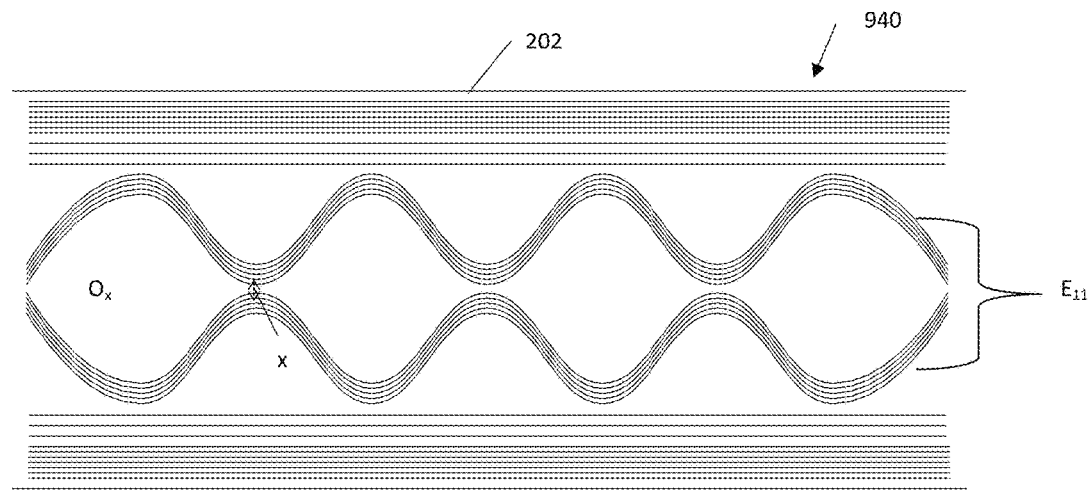
FIG. 9 is a simplified illustration of yet another alternative elastic composite web.

FIGS. 7-9 illustrate further embodiments of the elastic composite webs and distribution that can be achieved by and/or utilized, wherein like reference numerals are used to indicate like elements. Referring first to FIG. 7, the elastic composite web 740 includes an upper or backsheet material sheet (not shown) 712, a lower material sheet (not shown), but directly underlying the upper sheet 712 and multiple distributions of elastic strands. A distribution of elastic strands 710a, 710b is provided along each of the upper and lower edges 702, 703 of the web 740. These distributions ultimately make up the elastic annular region about the waist opening. Between these two distributions, two distributions 711a, 711b of variable elastics are provided (for the lower waist, crotch and leg regions). As in FIG. 3, these variably positioned elastic strands are distributed by means of the periodic, lateral motion of the elastic guides in FIG. 2, preferably to elicit a sinusoidal pattern. The first set 711a of elastics is distributed in a first sinusoidal pattern and are overlapped with the other set 711b of elastics distributed in a second sinusoidal pattern. In this exemplary embodiment, the first and second sinusoidal patterns are mirror images of each other. In this embodiment the degree of overlap "X" of the two elastic patterns is much smaller than that described in the embodiments relating to FIGS. 3 and 4. The resultant absorbent article made from this type of elastic distribution is described in FIG. 7, and features a greater amount of elastic material in the crotch region and less elastic material in a mid waist region.

FIG. 8 illustrates an alternate elastic composite web 840, wherein the degree of overlap or value of "X" is substantially zero or thereabout. The article 801 does not feature a crotch region 834 that is as broadly elasticized as that of the absorbent article 701 in FIG. 7.

FIG. 9 illustrates yet another, further embodiment of an elastic composite web 940 according to the present invention. This alternate composite web 940 employs an alternate variable distribution 911a, 911b of elastics. Specifically in this embodiment, the variable set 911a, 911b of elastic strands are distributed in a pattern in which the two sets do not overlap. In this example, the value of "X" is said to be negative. Although the patterns do not provide a series of completely annular elastic regions, the value of "X" is maintained sufficiently small so as to approximate a complete annular region, i.e., a substantially annular elastic region. By being substantially annular, the elastics about the waist opening and leg opening occupy more than 85% to 95% of the complete circle, and thus, the elasticity about the opening is practically continuous and substantially complete.

FIGS. 11A and 11B illustrate yet another elastic composite and disposable absorbent. The elastic composite is similar to that provided in FIG. 8. The overlap region dimension "X" has a value of zero, in that the two distributions 1111a, 1111b meet but do not completely cross. Instead, the two elastic distributions 1111a, 1111b form a broad, somewhat elongated concentration of elasticity at the center of the composite 1136. In the resulting disposable absorbent article, this feature translates to a concentration of all round elasticity in the crotch region 1134. FIGS. 11A and 11B are also provided to show exemplary dimensions of an elastic composite of the invention. The Figures also show preferred locations of certain element of the elastic composite 1136. For example, the core 1105 in this embodiment is located centrally over the concentration of elasticity discussed above, but is cut at a width that approximates the length of the elastic concentration discussed above.

FIGS. 11A and 11B also illustrate two stages in an alternative method of making a disposable absorbent article. FIG. 11A reveals a unitary elastic composite body 1136 that could have been freshly severed from a web of elastic composite, according to the invention Unlike earlier described finished elastic composites, the elastic composite 1136 has not had holes or sections cut therefrom (for later-formed leg openings). Instead, the elastic composite 1136 is folded in its full rectangular frame about longitudinal axis YY. The folded elastic composite 1136 then features quarter sections of the leg holes 1104 that may be cut or stamped out. Thereafter, the side edges 1106 may be sealed to form the leg openings of the absorbent training pants, according to the invention.

Gapping in the Elastic Distributions

The system and method of making an elasticized absorbent product may include a modified step of applying multiple distributions of elastics on the moving web. As described previously, in a preferred process, continuous distributions of elastics are applied generally in the machine direction. This includes applying and establishing at least two periodic or curvilinear distributions (generally in the machine direction) of elastics on the moving web by varying the lateral position of the elastics as the elastic distributions are advanced in the machine direction. Further to this step, continuous distributions of elastics may be applied to establish generally machine-directed distributions of elastic on each elastic composite body which have intermittent gaps (in the elastics). That is, a continuous, generally machine-directed distribution of elastic is applied, but the elastic strand on the finished composite web and on the final product is effectively segmented due to the intermittent gaps.

The locations of the gaps on the web are predetermined to correspond with desired gaps or absence of elastics in the final pants product. In some applications, the gap may be sufficiently wide to effectively de-elasticize the target area and in other applications, will be minimized to maintain continuity in the annular regions of elasticity in the final absorbent product. In one exemplary process, gaps in the elastic distributions are provided at locations on the web that correspond to the side edges of the pants product, whereupon the side seal or seams are formed. In yet another embodiment, gaps in the elastic distributions are located to coincide with the core location near the central or crotch region of the absorbent article. In this embodiment, it may be desired to disengage the core from the elastics and provide a relatively stable and unbiased core structure, or allow undisturbed placement of additional elements onto the core surfaces.

Elasticized or Profiled Core Structures

In the systems depicted in each of FIGS. 2 and 6, as well as that described in respect to the process illustrated through FIGS. 3 and 4, the core is delivered intermittently to the moving web pre-cut and oriented generally perpendicularly to the longitudinally moving direction of the moving web. As specifically shown in each of FIGS. 4 and 5, the pre-cut core is delivered on the web extending lengthwise between the longitudinal edges of the web, but in between each side edge (or severing line) of the elasticized composite. The core is, therefore, deposited in correspondence with its final location and orientation in the finished disposable absorbent product.

In many of the embodiments described herein, the inventive process is employed to apply a distribution of elastics across the width of each absorbent product, including over the core. The engagement or interaction between the elastics and the core may impart elasticity to the core, as required or desired by the design of the absorbent product. The resulting elasticized core may feature aesthetic and functional characteristics due to its elasticized regions. The benefits of elasticized core configurations have been discussed, for example, in U.S. Patent Application Publication No. US2011/0130736 A1, specifically FIGS. 6-9 in that publication (which application is assigned to an Assignee common with the Assignee of the present application and include, as inventors, one or more of the inventors named for the present application). One of the Figures is reproduced herein as FIG. 5 to illustrate an elasticated core structure 1801 (in a contracted state) achievable with the present inventive system and process. The core configuration includes a plurality of elastic distribution 1810 applied laterally in machine direction, and generally centrally on the moving web and across the core 1812. This previous patent application publication and specifically FIGS. 6-9 of the publication, and the descriptions accompanying those Figures, are incorporated herein for background purposes and made a part of the present disclosure. The common element in these referenced elasticized core designs is that elastics 1811 are directed and applied onto or proximate the core 1812 in the direction lateral to the lengthwise direction of the core 1812. In the present system and process, the application of elastics in the machine direction and centrally on the moving web, and the intermittent deposition of the core onto the web substrate in its ultimate position and orientation facilitate the provision of such an elasticized core. Moreover, the presently described system and process allow for variations in the elastic pattern applied to the core, including a plurality of different distributions or sets of elastics, spacing between the elastics, linear and/or curvilinear distribution patterns, including sinusoidal and other shapes.

The present system and process also allows for the cutting or gapping of the elastic distributions on the moving web and in the finished disposable absorbent product. In one embodiment, other curvilinear or periodic designs may be employed to distribute elastics about and proximate the periphery of the core and to encourage a pocket or cup shape in the core. The overlap of the two elastic distributions creates an annular elastic region along the periphery of the core, which can advantageously act as a type of O-ring seal. Such an elasticized O-ring may be designed in alignment with the user's bottom to improve absorption and retention. The elastic distribution shown in FIGS. 3-4 and 7-7A are two configurations suited for establishing such an annular elastic region and o-ring seal about the area of the core.

Several further variations in the process may be employed to engage the elastic distributions with the core. As discussed above, the elastic may not be applied directly to the core. For example, the elastic may be applied to the backsheet and situated between the backsheet and a second sheet or nonwoven. The resultant composite is then bonded with the core. With this composite, and specifically the backsheet directly engaging and connected with the core, the elastics within the backsheet composite act upon the core to create the desired elasticized and/or profiled shape. In another exemplary variation, the elastic may be applied to the backsheet and then the core is applied directly on top of the elastics (e.g., without an intermediate sheet). In any case, the elastic and sheet materials, and the core, are brought together on the form roller, and adhesive may be applied to the material sheets and elastics just before arrival at the forming roller.

In several of the core designs of FIGS. 6 and 7 in the referenced U.S. Patent Application Publication No. US2011/0130736 A1, the elastics are applied laterally and centrally on a rectangular core or in specific embodiments, in both or each of two overlapping cores. Elastication of the absorbent core structure, upon release of tension in the elastics, creates a narrowed central region of the elasticized core, which, as described in the referenced publication provides aesthetic and functional benefits in the absorbent product. In further embodiments, the spacing or pitch between successive elastics may be designed so as to create more of a concave narrowed central region. This may be achieved, for example, by placing a higher concentration of elastics along the center and a lower concentration away from the center (see e.g., FIGS. 7C-D in the referenced publication). The elastics may be strategically placed between a stack of cores and other materials to provide the profiled core configurations in FIG. 8 (of the referenced publication) as well as the corrugated configuration of FIG. 9 (in the referenced publication).

Elastic Composite Web Forming Mill

Figure 10:
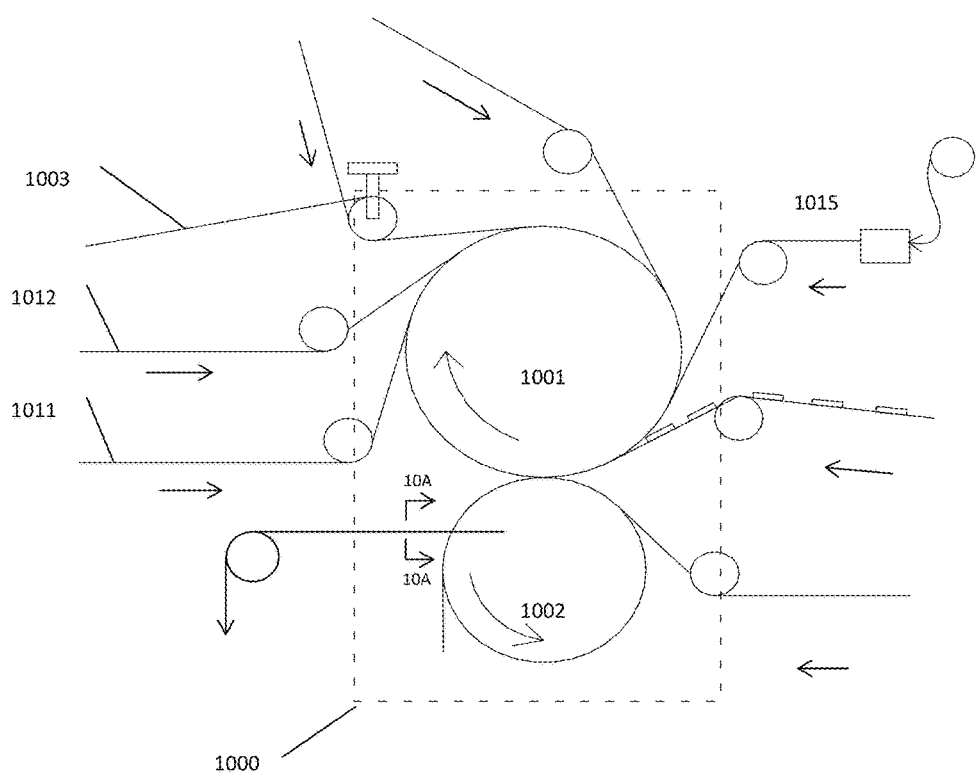
FIG. 10 is a simplified schematic representation of a system for making a disposable absorbent article.

FIG. 10 is provided as a simplified physical representation of a system 1050, and more specifically, an elastic composite web forming or joining mill 1000 of the system. The area (or region) inside the dashed box represents, in one aspect of the inventive system 1050, a centralized conglomeration of web components and system machine components, from which the desired web 1021 of discrete elastic composite bodies are outputted. The inventive system 1050 may be described as comprising a plurality of feed lines that converge on the joining mill 1000 in a predetermined manner to produce the predetermined moving web substrate 1021. The input feed lines are managed to direct a component of the product at a rate, speed, orientation, and lateral placement required of the web substrate product. Some input feed lines may be associated with "cut and place" units that intermittently apply a discrete unit of material to the moving web. Furthermore, the input feed lines are managed to converge and engage other input feed lines in the desired sequence and rate required.

With the system 1050 in FIG. 10, each of the elements of the web substrate is preferably applied to the mill 1000 linearly or inline in the machine direction. Accordingly, all feed lines and output lines can approach the mill 1000 from the right or left, or the top of the mill 1000, but within a lateral window not exceeding the axial length of the form roller 1001 (and, in some micro-applications, not substantially wider than the width of the web substrate 1021a). This physical characteristic of the system 1050 promotes manageability and flexibility in the process, including the ability to modify the properties of the finished absorbent product. The inventive system, and more particularly the mill 1000, also displays a small footprint. The mill 1000 also lends itself to being packaged as a modular, self-contained unit.

In one process, a web substrate product 1021a is outputted by the mill 1000 as shown in the lateral cross section of FIG. 10A. Upon output from the mill 1000, the moving web substrate 1021a comprises a layer of topsheet TS on the bottom, an AD (acquisition and distribution) layer above the topsheet TS, and a series of individual, elongated cores C above the AD layer AD. Above this, a sandwich is provided of an intermediate nonwoven layer NW, a layer of backsheet BS, and various elastic distributions E therebetween. Directional arrows in FIG. 10 indicate the direction toward which the composite web 1021a is folded. As shown, the web 1021a is folded such that the topsheet layer TS rotates toward itself and is ultimately positioned on the inside of the folded web. In the finished absorbent article as worn, the topsheet TS is placed adjacent the body of the wearer.

After emerging from the mill 1000, the web substrate 1021a may be folded, sealed, and cut to produce the disposable absorbent article. These subsequent steps are considered post-joining steps that are implemented after delivery or output of the web 1021a. The folding step is performed at a folding station 1022 comprising of angular directional bars that are located immediately forward of rollers 1001, 1002. The folding station 1022 directs the web 1021 to a series of turns that flips and folds the substrate 1021a. Once folded, the leg holes are cut out, the side seams are sealed together, and then, the web substrate is severed along the seams (to produce discrete pants products). These steps have been discussed in respect to FIGS. 4 and 5, for example. Additional, pre-packaging steps may also be employed after the sealing and severing steps. In alternative embodiments, the step of cutting or punching the leg cutouts may be provided before the folding station 1022 and immediately after delivery of the web substrate output 1021a.

Referring now to FIG. 10 and well as FIG. 10A, several stages of the joining process are described as a sequence of joining various components of the web substrate 1021a. The primary components of the mill are a main or forming roller 1001 and a corresponding secondary roller 1002. As shown in FIG. 10, an input feed 1011 of backsheet material is engaged by the forming roller 1001 as well as the distributions 1012 of waist elastics and distributions 1001, 1003 of curvilinear elastics (as previously described in more detail in respect to FIGS. 2A and 2B). The moving web of elastics applied to the backsheet is then engaged from above by an input feed 1014 of intermediate nonwoven. This engagement sandwiches the elastics within the backsheet and intermediate nonwoven. In further embodiments, a cutter roller may be added to engage the form roller and to selectively cut one or more of the elastic distributions sandwiched by the backsheet and intermediate nonwoven.

The resultant elasticized web then engages the input feed 1016 of spaced apart and laterally oriented cores. As described previously, the cores are spaced in correspondence with a central position on the final pants product and in alignment with the longitudinal centerline of the moving webs and the forming roller 1001. The cores are preferably delivered pre-cut in an elongated rectangular form that is lengthwise to the longitudinal or machine direction. A cutting roller machine 1027 is provided upstream of the rollers 1001, 1002 and receives a continuous feed of sheet core material from a supply roll 1029. Preferably, a second input feed 1016 of a second core or an ADL layer is directed atop and upon the resultant elasticized composite (with core). In this instance, an input feed 1017 of the topsheet engages the elastic composite (with cores) to provide a topsheet layer over the core material(s). The resultant product is a moving web substrate 1021 of an elasticized absorbent composite that may be further processed to produce a pants product or a diaper product.

In this system configuration, the web substrate 1021*a* is delivered with the backsheet BS on top and the topsheet TS on the bottom. The continuous web 1021*a* is the preferably passed to the folding station 1022, which effectively flips and folds the web 1021*a*. From there, the side seams of the web 1021*a* may be sealed and then severed, to produce discrete elastic composite bodies.

Reversed Elastic Composite

An alternative disposable absorbent product may be produced by the system and process by modifying the input feed lines to the joining mill 1000. Such an alternative moving web substrate 1021*b* of elasticized composite bodies is depicted in FIG. 10B in lateral cross-section. The moving web 1021*b* outputted by the joining mill 1021 provides a topsheet layer TS as a top layer and multiple distributions of elastics E sandwiched between the topsheet layer TS and an intermediate nonwoven layer NW. The core C, the ADL layer AD, and the backsheet layer BS fill out the rest of the elastic composite. Referring to FIG. 10, such a composite web 1021*b* may be achieved by switching, for example, the topsheet feed 1017 with a backsheet source and perhaps, as necessary switching the ADL and core input feed sources. Finally, the resultant web substrate is folded in the reverse direction (see fold directional arrows) such that the elastic distributions E are inside of the core C. By placing the elastics closer to the user, the topsheet TS is drawn closer to and about the body of the wearer and the elasticized composite 1021*b* will tend to support and accommodate the contour of the wearer's body. The improved engagement of the topsheet TS about the wearer not only enhances fit, but the topsheet TS is better positioned to prevent leakage. In further embodiments, the inventive process may be employed to apply sinusoidal or other curvilinear elastic distributions about the periphery of the core, thereby creating an elasticized pocket about the topsheet/intermediate nonwoven sub-composite or the core. The incorporation of such an upwardly biased pocket may also be conducive to the use of one or more central apertures for disposal into the space between the core and the topsheet/intermediate nonwoven.

Disposable Absorbent Article with Reusable Outer Shell and Disposable Absorbent Core Insert Disposable Absorbent Core Insert FIGS. 16-23 illustrate preferred variations of a disposable absorbent core insert 1910 suitable for engagement with an outer shell, according to the disclosure (wherein like elements are indicated using like reference numerals). FIG. 25 illustrates incorporation of any one of the core inserts 1910 with an outer shell according to the present disclosure. These preferred core inserts 1910 are elasticated to provide a desired shape and enhance engagement and retention by an outer shell. Referring first to FIGS. 16-18, the basic disposable core insert 1910 may include a back sheet 2014, a permeable topsheet 2018 (shown in FIG. 16 but cut out in FIGS. 17 and 18 to reveal the core layer 2016 and back sheet 2014) and an absorbent core layer or core section 2016 disposed therebetween. The material layers 2014, 2018 are, in most applications, sourced from a non-woven sheet. Optionally, the core insert 1910 may also contain an ADL layer, tissue layer or nonwoven sub-layer.

Typical topsheet or top layer material suitable for the core insert include a water permeable nonwoven, made from polypropylene or polyethylene fibers, or spunbond material. The topsheet material may also be provided by an apertured nonwoven or an apertured film. Suitable backsheet or bottom layer material for the core insert include a water impermeable sheet, such as a polyethelene film or composite of a polyethylene film and nonwoven (which may be breathable or non-breathable). Also suitable for the backsheet material is a very highly hydrophobic nonwoven material (with a high resistance to water flow through the material (hydrohead test)).

The constituency of the absorbent core layer 2016 may be provided by cellulose fluff pulp and SAP, airlaid or cellulose free core. More detailed examples of suitable absorbent core constructions or composition may be found in the following patent publications: U.S. Pat. Nos. 6,794,557; 8,148,598; U.S. Pat. Appl. Publ. No. US 2012/0175056; U.S. Pat. Appl. Publ. No. US 2014/0180230; U.S. Pat. Appl. Publ. No. US 2014/0276508; U.S. Pat. Appl. Publ. No. US 2014/0303582; and U.S. Pat. Appl. Publ. No. US 2015/0045756. Each of these publications is incorporated herein by reference in its entirety and made a part of the disclosure. Further, the composition of the absorbent core layer may be further formulated and configured to achieve a desired stiffness, preferably in target areas such as a central region to achieve and promote a desired shape as further discussed above. Moreover, the absorbent core layer may be supplemented by a stiffening construction or stiffener material preferably placed adjacent the target regions (discussed further below). For example, the stiffening material may be provided by air laid cellulose material or high basis weight nonwoven, and may be circular or rectangular in shape, or applied in strips. The stiffening material is centrally placed in most applications and provides increased longitudinal rigidity.

The core composition may also be formulated to provide regions that function as stiffeners. For example, certain regions may be provided with more absorbent particles (SAP) or a higher density absorbent material. Alternatively, such regions of absorbent composition may supplemented with other particles, fibers, or other material layers thereby increasing the density, thickness, or hardness of the target region. In some embodiments, hot melt adhesive may be provided or increased in the target regions.

Suitable materials for the deployment of stiffeners in the core insert include high basis weight nonwoven, an airlaid cellulosic material, and a wetlaid cellulosic material. Stiffeners or stiffening regions may also be formed by compressing regions of the absorbent core insert. In further embodiments, the core insert may be provided with zones of different compression, which yield different degrees of stiffness (e.g., as employed in a fluff-SAP type core). A stiffener provided by a higher basis weight region of the core may be formed by adding more SAP, more nonwovens or more hotmelt adhesive in the area of interest.

Stiffeners may be used in any part of the core insert to either promote a flat appearance in a certain area, or promote folding in a region (along fold lines) between two stiffeners. In certain embodiments, stiffeners are preferably located in the central target area (to resist bending along the core centerline(s) or centerpoint. Alternatively, two stiffeners may be located on either side of the center line (typically, lateral centerline) of the core so as to promote folding along the desired regions or fold lines, which will coincide with the gap between the two stiffeners (see e.g. FIGS. 23, 37A, and further discussions below).

The core layer may also composed of pockets or aggregates of superabsorbent particles as known in the art. The shape and size of these pockets, as well as their compositions, may be varied in different regions of the core layer to achieve certain stiffness and bending characteristics. The pocket patterns, as determined by the bonding patterns, may be designed to achieve the specific stiffness properties. Furthermore, the bonding method (e.g., point bonding, solid bonding, etc.) may also be varied. See e.g., U.S. Pat. Appl. Publ. US 2014/0303582 A1 and U.S. Pat. No. 8,148,598.

The disposable core insert 1910 is preferably of a rectangular (see e.g. FIGS. 16 and 17) or hourglass shape (see e.g. FIG. 18), influenced by the presence of a number of elastic strands 2020 established between the topsheet 2018 and backsheet 2014, as well as the incorporation of stiffening constructs or materials. Preferably, one to three elastic strands are disposed about, adjacent, or proximate on side of the core layer or core section. The elastic strands 2020 are disposed generally along and generally parallel with the long sides of the absorbent core layer 2016. The elastic strands 2020 may be disposed straight-wise or straight (parallel to the sides of the core as in FIGS. 16-18) so as to form standing gathers or cuffs at the sides of the core only. The elastic strands 2020 gather and lift the materials (i.e. nonwoven topsheet and backsheet) around the side and end margins of the core insert. The result is a standing cuff at the sides and, in some designs, the ends of the core insert 1910. See e.g. FIG. 23. More preferably, the elastic strands 2020 are shaped, by applying the strands in curved configurations, such that the cuff at the front and rear of the core insert curves inwardly, as shown in FIGS. 19-21. In other designs, the elastic strands 2020 may be curved further so as to substantially or completely encircle the absorbent core layer 2016 and the resulting standing cuff surrounds the absorbent core layer 2016, as shown in FIGS. 22A-22C and FIG. 23. Completely surrounding the absorbent core layer, the resulting leg gather provides a continuous leakage barrier along the sides, front and rear of the absorbent core insert, which helps to preserve multiple use of the outer shell.

FIGS. 16-18 illustrate absorbent core inserts 1910 featuring combinations of elastic strands 2020 and specifically shaped absorbent core layers. FIG. 16 shows the topsheet 2018 partially cut away to reveal the backsheet 2014, core layer 2016, and elastic strands 2020 below. FIGS. 17 and 28 show the core insert 1910 with the topsheet 2018 completely cut away to reveal a full view of underlying core insert components. (See also FIGS. 13-15 for a cross-sectional view illustrating the relative disposition of the basic components of the core insert 1910). The elastic strands 2020 in the illustrated applications are disposed straight-wise and spaced from and along the long side of the core layer. FIGS. 19-21 show absorbent core inserts employing curved elastics strands 2020. In some of these applications, the elastic strands 2020 may actually contact or engage the absorbent core layer 2016 (either on the backsheet side or topsheet side). FIGS. 22A-22C provide a further variation of the absorbent core inserts wherein the curved elastic strands on either side of the core layer 2016 come together. In the configuration depicted in FIGS. 22A and 22B, the elastic strands 2020 intersect or meet at or near the top and bottom ends of the absorbent core layer 2016 (end regions of the core insert) to substantially surround and encircle about the core layer 2016. Such elastic elements are typically directed and deposited on a moving web in the generally longitudinal direction (of the absorbent core composite) and periodically varied (laterally) while being deposited to achieve the desired pattern and curvature. The elastic strand may be applied on the moving web containing the backsheet material and prior or after deposit of the core layer on the web). In FIG. 22C, the elastic strands 2020 meet or intersect at a central location on either side of the core layer 2016 (away from the top or bottom end regions). These elastics are typically directed and applied on the moving web in a direction lateral to the longitudinal length of the core insert.

In the applications according to FIGS. 22A-22C, portions of the elastic strands 2020 are in contact with or may be applied directly beneath or atop the core layer 2016. As explained further below, the extent and location of engagement between elastics and the core layer ultimately impacts the shape and bias of the core insert and its retention within the outer shell.

In alternative applications, the elastic strands may be spaced further outwardly of the perimeter of the core layer. The absorbent core insert 1910 of FIG. 23A is such an application, and also a variation of the elastic configuration in FIG. 22C. The elastic strands 2020 are spaced away from the perimeter of the core layer 2016 and encircle the core layer 2016. As shown in the perspective view of FIG. 23B, tension in the elastic strands 2020 form leg gathers 2022 on either side of the core layer 2016 and further, raises the backsheet and\or topsheet material of the core insert 1910 above the core layer 2016 to create a standing barrier 2024 all the way around the core layer 2016. The end regions above and below the core layer features a dam-like structure 2026 formed by the gathered materials (e.g., gathered top sheet and back sheet material). The elastics 2020 also bias the end region inwardly further contributing to the creation of a cup or bucket shaped core section and absorbent core insert.

Figure 28A:
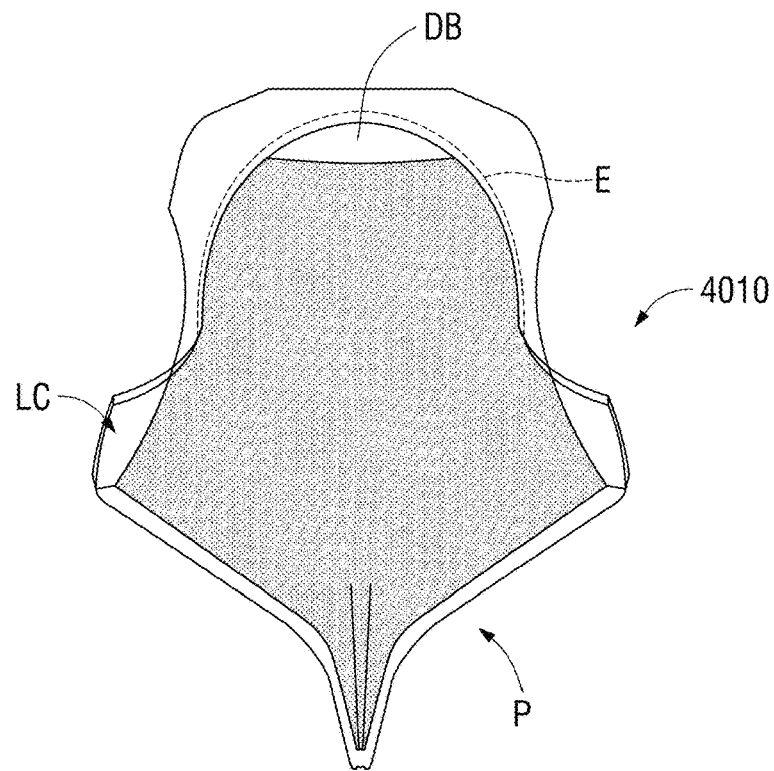
FIGS. 28A and 28B are lateral cross-sectional, elevation views of a core insert with a formed bundle or plug for receipt by a retainer or receptacle of a corresponding outer shell, according to the present disclosure.
Figure 28B:
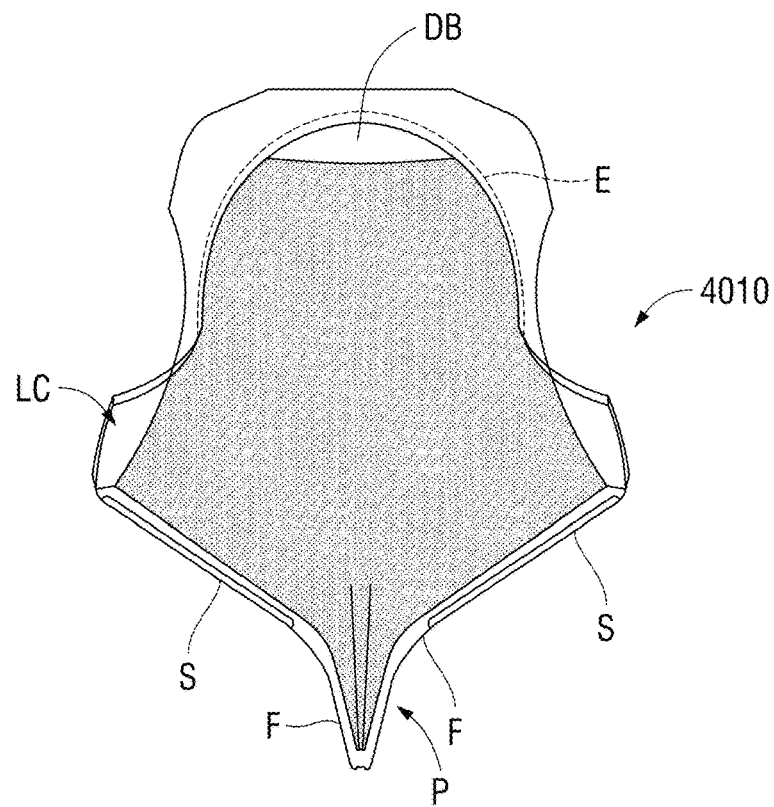
Figure 31A:
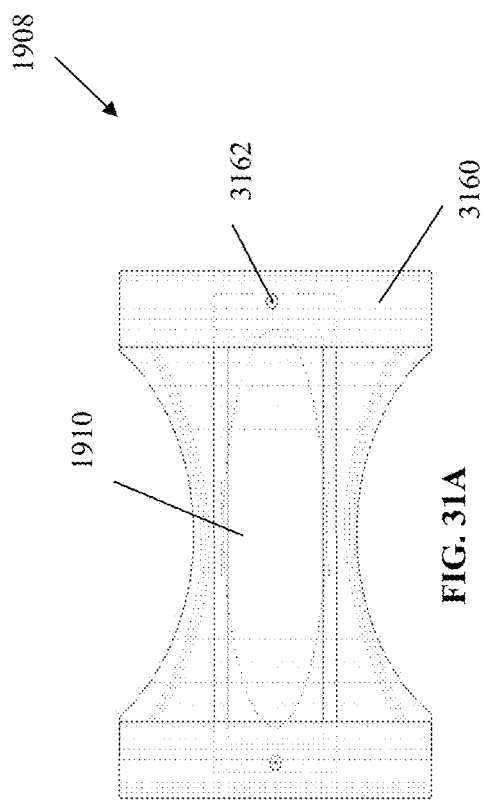
FIGS. 31A-D are simplified plan views of a disposable absorbent article equipped with folded end regions with snap fasteners and a disposable absorbent core insert detachably retained therein.
Figure 31B:
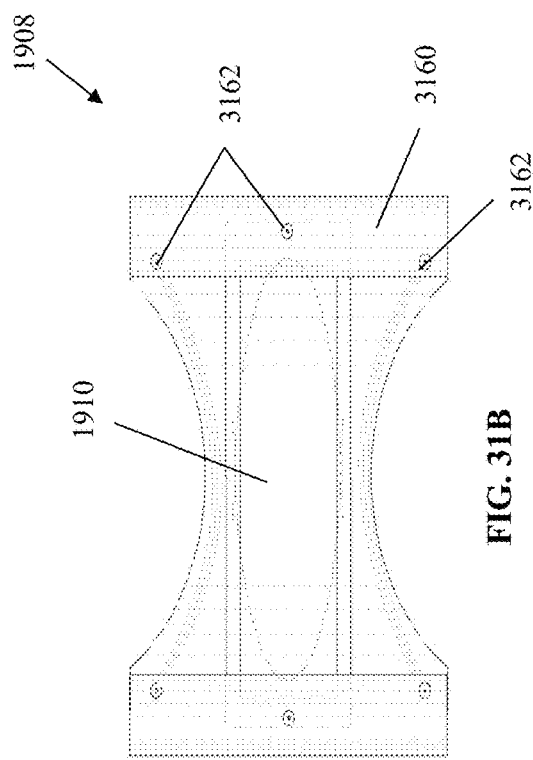
Figure 31C:
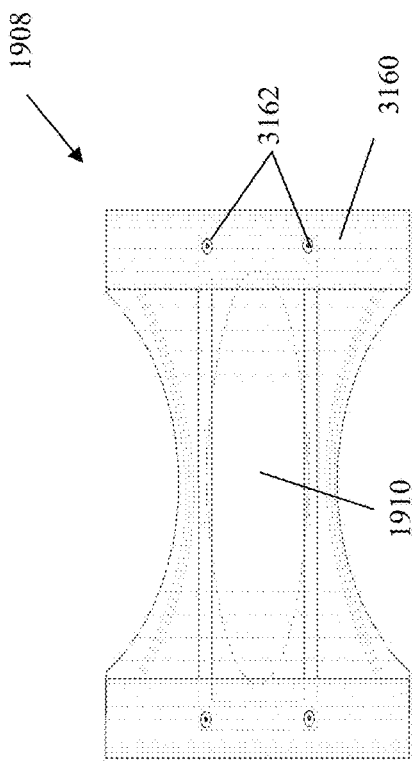
Figure 31D:
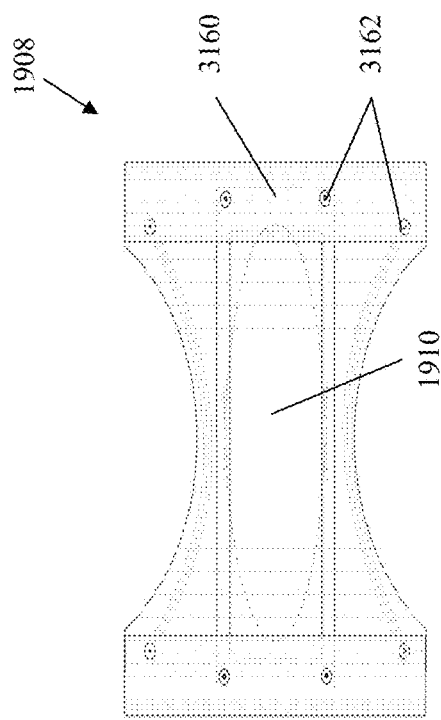

Preferably, the elastics (e.g., elastic strands or filaments) in the core insert are sandwiched between two material sheet layers (topsheet and backsheet) and, along the side and\or end margins, are connected to both layers. Accordingly, the elastics will act to contract to a smallest possible length. Referring to FIG. 23A, a shorter length of elastic is achieved during contraction, when the end or side margins move out of the plane of the absorbent core layer or section and rise up over the core to form a smaller loop of elastic (see FIG. 23B; FIGS. 28A-28B).

FIG. 24 is a perspective view of an elasticized absorbent core insert 1910 employing the elastic configuration illustrated in FIG. 22C. As depicted in FIGS. 24A and 24B, portions of the elastics 2020 are disposed beneath the core layer 2016 and adjacent the backsheet 2014 (or base layer), while portions along the sides are spaced away from the core layer 2016. The side portions rise above the core layer 2016 and also lift the materials of the top sheet 2018 and backsheet 2014. The end portions of the core layer 2016 are raised and bias the end regions of the core insert 1910 inwardly toward each other. This results in a cup-shaped absorbent core insert with a circular raised perimeter 2024 formed by the side leg gathers 2022 and the raised end regions. The circular standing cuff 2024 provides a continuous leakage barrier around the core layer 2016.

As suggested above, stiffening constructs may be incorporated to achieve a desired shape of the core layer and the overall shape of the core insert. Stiffeners may be applied or positioned in or proximate the center of core section 2016 in FIGS. 23 and 24, for example, to provide resistance to the biasing action of the elastics and promote bend or shaping about the center of the core layer. Furthermore, such stiffeners may also facilitate formation of a protuberance used in securing the core insert 1910 to the outer shell 1912, as further described below (and as shown and described in respect to FIG. 23E also).

Figure 23C:
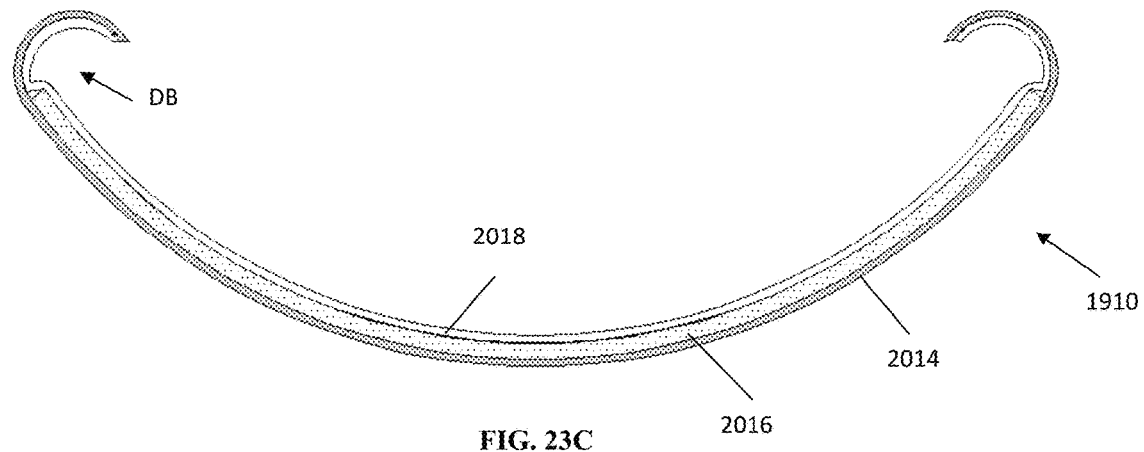
FIG. 23C is a longitudinal cross sectional view of the disposable absorbent core insert (leg cuff left out intentionally)
Figure 23D:
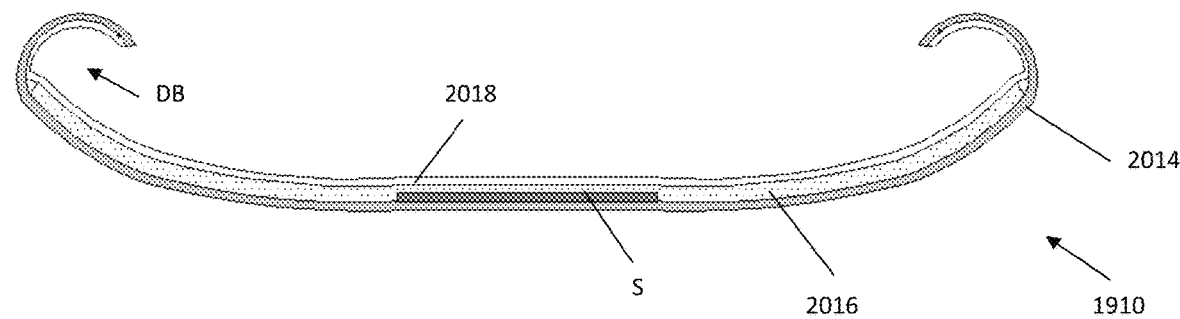
FIG. 23D is a longitudinal cross sectional view of the disposable absorbent core insert in FIG. 23C equipped with a stiffener construct directed along the longitudinal or machine centerline (leg cuff left out intentionally)
Figure 23E:
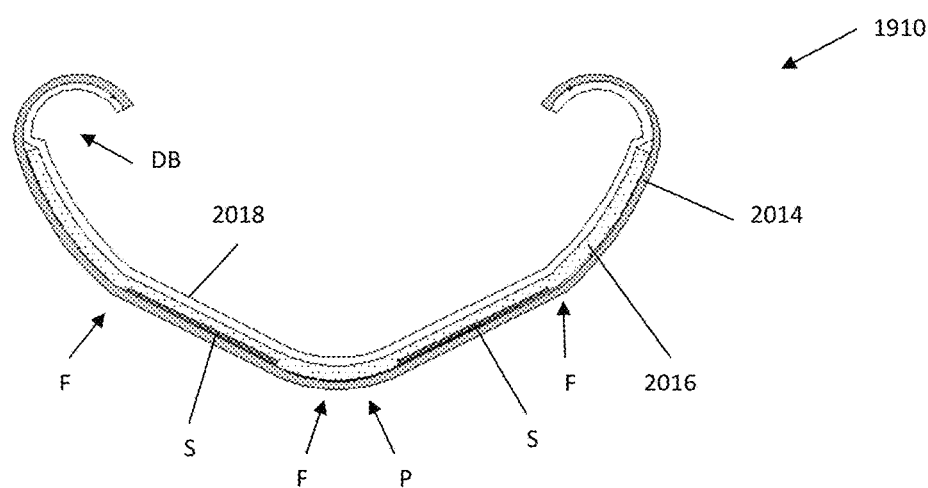
FIG. 23E is a longitudinal cross sectional view of the disposable core insert equipped with a pair of spaced apart stiffener constructs directed in the longitudinal or machine direction (leg cuff left out intentionally)

FIGS. 23C-23E provide cross-sectional elevation views of exemplary elasticated disposable core inserts 1910, highlighting the curved and end-biased profile of the core insert 1910 (leg cuff alongside margins are left out intentionally). The core insert 1910 typically includes a nonwoven top layer 2018, a nonwoven bottom layer 2016, and an absorbent material layer or section 2016 sandwiched therebetween. In FIG. 23D, the core insert 1910 is fitted with a single stiffener S (of a material stiffer and harder than the nonwoven layers and the absorbent core layer). The region of the stiffener S is relatively flat, as compared to that in FIG. 23C, but the elasticated core insert maintains a curved profile and raised end regions (dam barriers, DB). In FIG. 23E, the core insert 1910 is equipped with a pair of spaced apart stiffeners S. The placement and juxtaposition of the stiffeners S causes regions of relative weakness that become fold lines or fold regions F. In this embodiment, the two stiffeners S also help to shape a central protruding portion P (or protuberance, which is defined as a part that projects or protrudes outward from the rest).

FIGS. 28A and 28B are exemplary lateral cross sectional views of a core insert, such as that of FIG. 23A, according to the disclosure (wherein like elements are indicated by like reference numerals). Both Figures illustrate a loop of elastic (s) (E) disposed about the absorbent material layer of the core insert to create an all-around raised leg cuff (LC), including dam barriers (DB) at the end regions. FIG. 28B illustrates the further use of stiffener (S), spaced apart in the lateral or cross machine direction to help create a pair of folds (F). The folds (F) help create the bundle or plug (protuberance or protrusion) (P) that is insertable in a retainer clip in the outer shell. The bundle or plug is then removably attached or retained to the retainer clip receptacle, thereby removably attaching the core insert with the outer shell.

The curved elastics shown in FIG. 23 may be applied borrowing processes and techniques described previously in respect to FIGS. 1-11. In such processes, an elastic feed system is moved laterally (relative to the longitudinal or machine direction of the web) to establish elastic distributions on the web that periodically come close together or intersect to form a series of annular regions. For example, the elastics may be applied to establish a sinusoidal pattern. In these applications, the extent of lateral displacement must be sufficient to clear the core section. The regions at which the elastics intersect are positioned periodically between the position of core section application.

The curved elastics shown in FIGS. 21, 22, and 23 may also be applied borrowing processes and techniques described previously in respect to FIGS. 1-11. It should be noted, however, that the elastics may be applied in the cross machine direction as opposed to the machine direction previously described. In the alternative, certain components or the entire composite bodies that make up the web being processed may be oriented 180 degrees from the orientations previously illustrated, with the required distribution of elastics strands also applied in the machine direction.

Outer Shell

FIG. 25 illustrates how the core insert 1910 may be readily attached to or detached from an outer shell 1912. The combination depicted is a semi-enclosed training pants 1906. The core insert 1910 is received within the shell 1912 of the garment 1906, but may be readily detached therefrom by separating the core insert 1910 from the shell 1912 and removing the core insert 1910 through a waist opening 1990 of the garment 1906.

FIGS. 26-30 show variations of an outer shell 1912 suitable to receive and retain disposable absorbent core insert 1910 according to the present disclosure. The outer shell is designed for reuse with a number of absorbent core inserts (at least 10-30). As such, the outer shell is made from more durable materials than the insert. Suitable materials include higher basis weight polypropylene or polyethylene nonwovens (>20 gsm) or natural materials such as cotton nonwovens or jersey fabrics. In one embodiment, the outer shell is constructed from at least two layers of synthetic nonwovens and a number of elastic strands disposed between the two layer. Preferably, the elastic strands are distributed to provide elastication around the waist and leg openings. Such elastic strands may be established between the two layers as described above in respect to FIGS. 1-18. Alternatively, the outer shell may be shaped by folding and adding darts.

The outer shell may be constructed from a washable material such as a cotton jersey fabric. In such an embodiment, the outer shell resembles a garment and could feature elastic materials, folds, seams and darts to create a suitable shape and a good fit.

The outer shell 1912 of the disposable absorbent assembly 1908 in FIG. 26 features multiple elastic distributions, including a set of elastics 2636 straddling each waist region and a set of elastics 2638 about each leg opening (as previously described herein). The core insert 1910 is situated in the crotch region between the waist regions and the set of elastics 2638 about the leg openings. In this configuration, only a few widely-space elastics of the waist elastics lay beneath the core insert 1910. Most of the core insert 1910 sit on a region of the outer shell 1912 free of elastics. The core insert 1910 is equipped, however, with laterally (i.e., lateral to the longitudinal length of the outer shell 1912 and core insert 1910) traversing elastics 2620 that encircle most of a core layer 2616. These encircling elastics 2620 help promote the cup or bucket shape of the core insert 1910 as previously described in respect to FIG. 24.

Figures 27A, 27B:
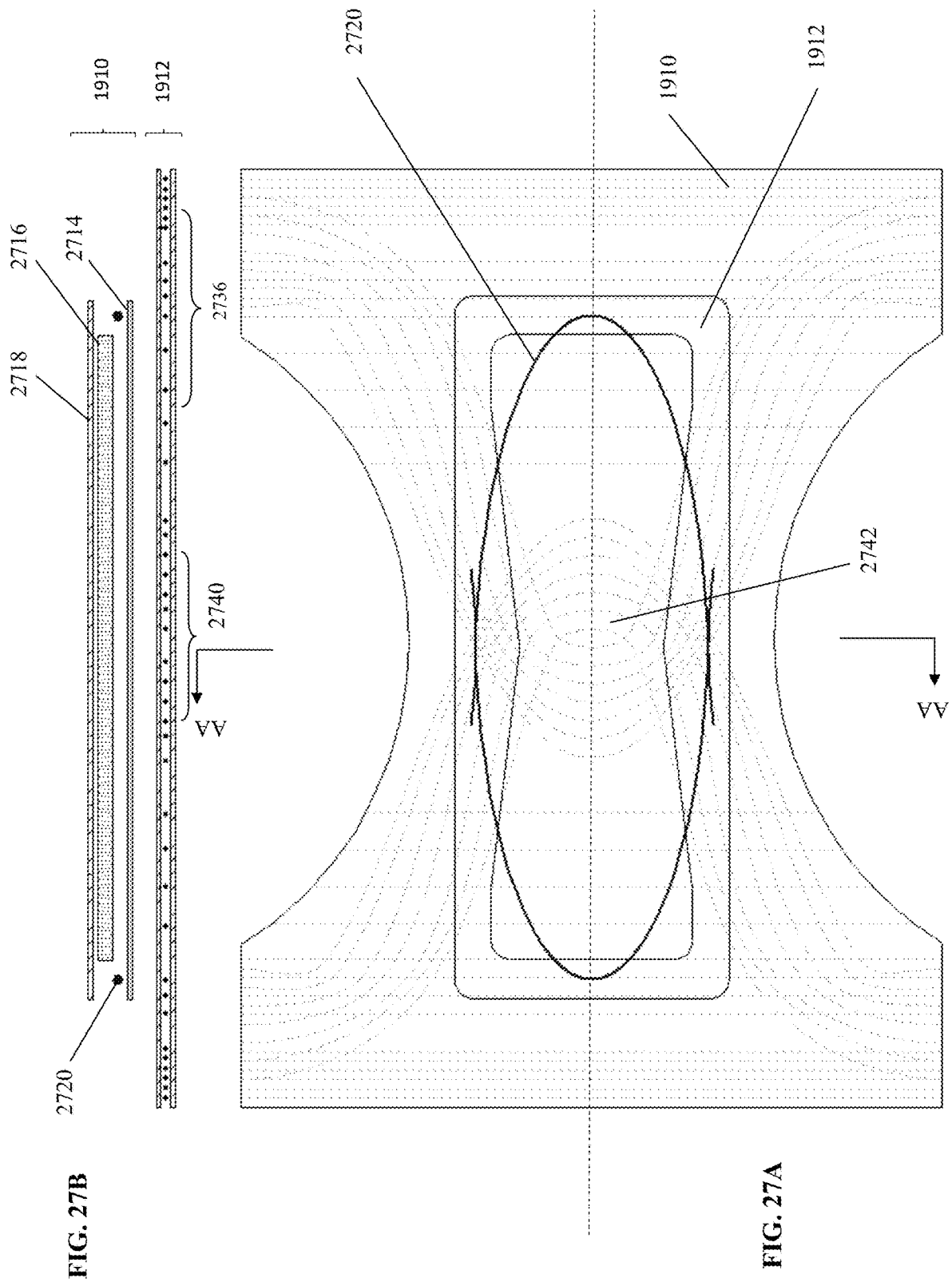
FIGS. 27A and 27B show a plan view of yet another alternate disposable absorbent article incorporating a detachable disposable absorbent core insert, in a flat, laid-open configuration.

In the disposable absorbent assembly 1908 of FIGS. 27A and 27B, the outer shell 1912 feature multiple alternate sets of elastic distributions, including waist elastics 2736 and a pair of elastic distributions 2740 that traverse across the middle of the outer shell 1912. The elastics 2740 intersect and form a small elasticated annular region 2742 that ultimately occupies the center of a crotch region. The core insert 1910 is centered upon this annular region 2742. This centralized elasticated annular region 2742 also facilitates shaping of the outer shell 1912 to receive and retain a specifically shaped core insert 1910 therein.

Annularly arranged elastic(s) in the outer shell (chassis) advantageously form a loop around a central area of the outer shell material. As the elastic loop contracts, there is an excess of material inside the loop that bulges or protrude outward to form a cup-shape or bag (a receptacle), into which a removable male counterpart on the core insert, i.e. a removable insert plug, may be received. Preferable designs will have a larger "annular loop region." (See e.g., the elastic configuration in FIG. 7). The size of the loop will correspond to the size of the insert plug (so that the insert fits snugly inside the cup created by contraction of the annular loop elastics. The elastic loop and the receptacle formed therein forms part of the retaining structure, retainer, or receiver in the outer shell for removably or detachably engaging (attaching) with the core insert (as further described below).

Readily Detachable Absorbent Core Insert

As a key feature of the absorbent core insert-outer shell combination is a means of securing the disposable core insert to or within the outer shell. Such securement means may borrow from prior art solutions employing hook and loop systems or adhesive. For example, three to five hook fasteners may be disposed on the outer surface of the backsheet of the insert which are engage able with loop fasteners on the outer shell. Alternatively, the hook fasteners may be disposed on the inside of the outer shell and configured to engage with aligned loop fasteners on the disposable core insert. In one set of embodiments, the loop fasteners are provided by a nonwoven material that completely covers either the outer surface of the backsheet of the core insert or the inner surface of the outer shell. Elastic strands may be deployed in these areas to gather the nonwoven material and create an enhanced loop fastener (by increasing the surface area of the loop material). Notably, the elastic strands also advantageously impart stretch and elastic properties in the same areas. Alternatively, snap buttons (poppers) may be used to secure the core insert to the outer shell. These fasteners may be positioned in each of the four corners of the absorbent core insert and aligned with a receiving fastener on the outer shell.

In further embodiments, other means are employed for readily engaging and securing the absorbent core insert in or to the outer shell. In some applications, hook and loop fastening systems or snap buttons may still be used as supplemental means for stabilizing the absorbent core insert within the outer shell. For example, a hook and loop system may be located centrally or at the end regions between the absorbent core insert and outer shell, while other means are employed at other regions.

In one set of embodiments, a small soft clip is mounted inside or outside of the outer shell. Referring to FIG. 13, such a soft clip 2850 on the outside of the outer shell 1912 and form a depression or receptacle 2852 near the center of the outer shell 1912. The clip may be formed from a soft silicone material, or a dental gel type material. As suggested above, elastics incorporated within the outer shell 1912 may be located to enhance or promote the shape or focus of the receptacle 2852. FIG. 14 depicts a core insert 1910 equipped with a protrusion or protuberance 2854 with an elongated shape to correspond with the shape of the receptacle 2852. Typically, the desired shape of the absorbent core insert 1910 is achieved through strategic placement of elastic strands. For example, elastics disposed in the absorbent core insert in a sinusoidal pattern or along the machine direction may configured to create a U shape in the center of the insert body.

As illustrated in FIG. 15, a protuberance 2854 formed in the absorbent core insert 1910 readily fits into and conforms with (e.g., plugs into) the receptacle 2852 in the center region of the outer shell. The corresponding shape in the outer shell is similarly created by the establishing a specific elastic configuration in the outer shell.

In further embodiments, the absorbent core insert may be shaped (e.g., locally) differently or at alternate locations so as to readily align and engage or conform with a correspondingly shaped outer shell or component or region of the outer shell. Furthermore, such securing means may be supplemented by hook and loops systems, securing flaps and\or fasteners for receiving and retaining the core insert within the outer shell. In any such design or combination of designs, consideration must be given to providing a smooth and comfortable surface of the core insert for contact with the wearer. Also, the core insert should be preferably be easily and readily attachable to, and detachable from, the surface of the outer shell (i.e., to facilitate handling and consistent placement, and minimize occurrences of spillage during replacement of the core inert).

Alternatively, the outer shell may be folded and elasticized to create flaps at opposite end regions as shown in FIGS. 29-32. The flaps receive and retain the front and rear edges of the absorbent core insert, thereby securing core insert within the outer shell. FIGS. 29A and 29B illustrate one variation of such a flap 2960 formed by folding an end edge of one or both of the material layers of the outer shell 1912 inwardly. The flap receives and holds the end of the core insert in place. In this example, snap fasteners 2962 are used to maintain the ends of the flap 2960 while maintaining a gap in between for receipt of the core insert 1910. To remove and dispose of the core insert, the ends of the core insert is simply slipped out from under the flap and\or the snap fasteners may be unfastened. Other securing means such as adhesive and a hook and loop system are also contemplated for use. The flap may also be equipped with elastics that stiffens and\or biases the flap inwardly to retain the core insert. Notably, the flap may also provide a dam or barrier that helps to contain leakage from the core insert.

In the embodiment illustrated by FIGS. 30A and 30B, flaps 3060 are created by excess material in the topsheet or top material layer of the outer shell. The flap 3060 is elasticated by a plurality of elastics situated in the fold and is biased inwardly (toward the core insert 1910). In the embodiment depicted, there is sufficient bias or tension in the flaps 3060 to hold the end regions of the core insert 1910. Thus, no additional securing means are incorporated into the flap 3060 or outer shell 1912.

Figure 32B:
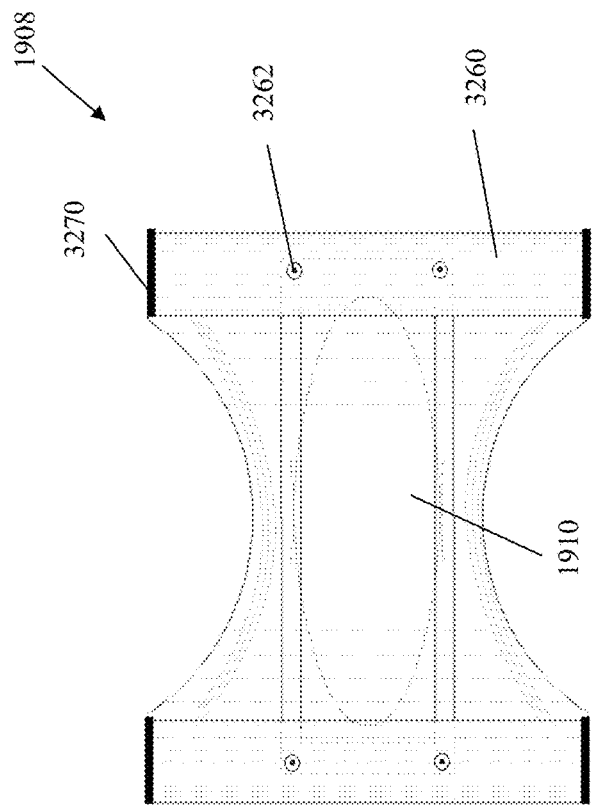
FIGS. 32A-B are simplified plan views of a disposable absorbent article equipped with further variations of folded end regions and a disposable absorbent core insert detachably retained therein.
Figure 32A:
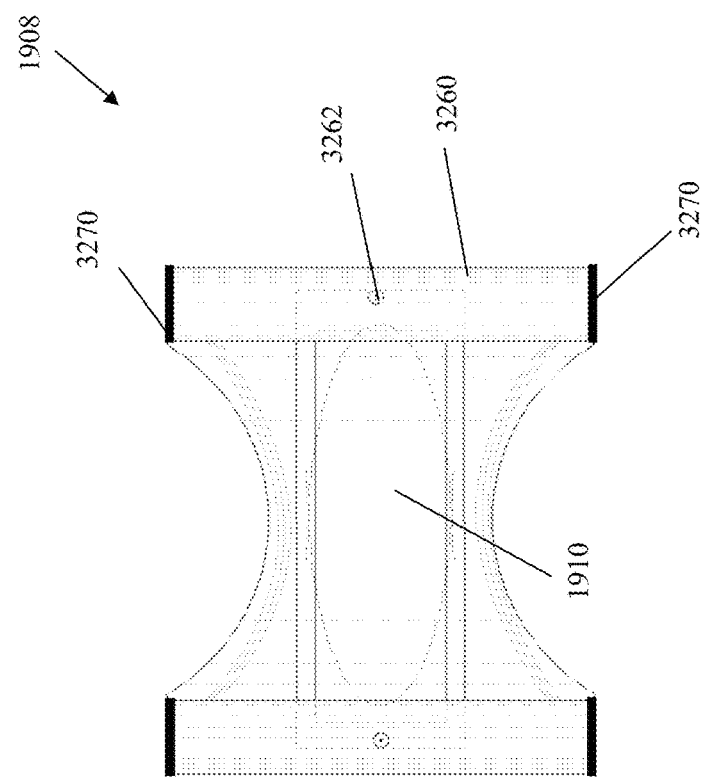

FIGS. 31-32 illustrate alternate flaps 3610 incorporating snap fasteners (wherein like reference numerals are used to indicate like elements). In FIGS. 31A-31D, snap fasteners 3612 are employed but one or more of the fasteners are located more inwardly toward the center of the flap to effect a more reliable grip on the core insert. In the embodiment illustrated by FIGS. 32A-32B, the ends or peripheries 3270 of the flaps are welded or bonded so as to set the folded configuration.

In addition to the above, a clip or some other alignment of product shape and elastics could serve to hold the insert in the center of the product. It should be apparent, therefore, that a combination of securement means may be employed to achieve the desired stability and\or ready and easy receipt of core insert within the outer shell, with cost and manufacturing considerations also accounted for.

Figure 33C:
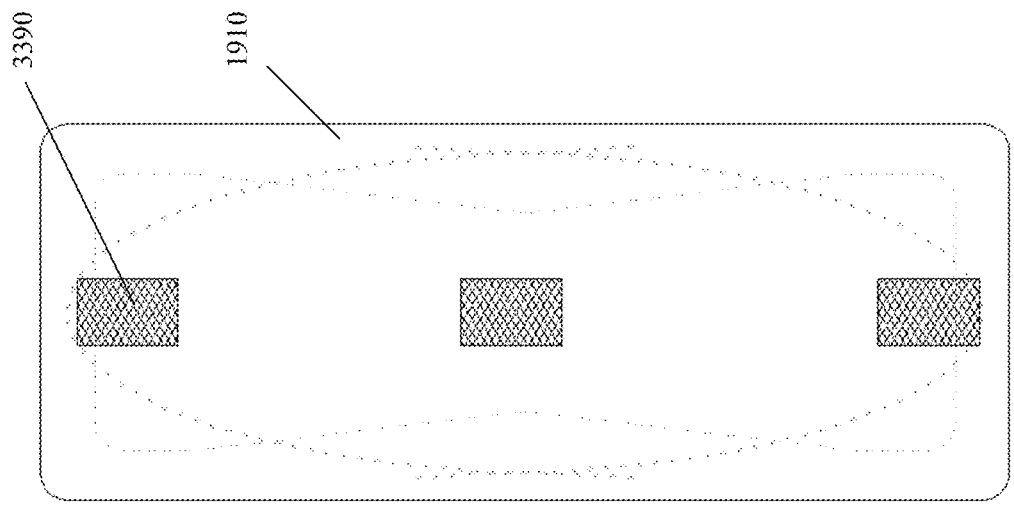
FIGS. 33A-33C are plan views of disposable absorbent core inserts showing locations of hook patches or regions on a backsheet of the core insert.
Figure 33B:
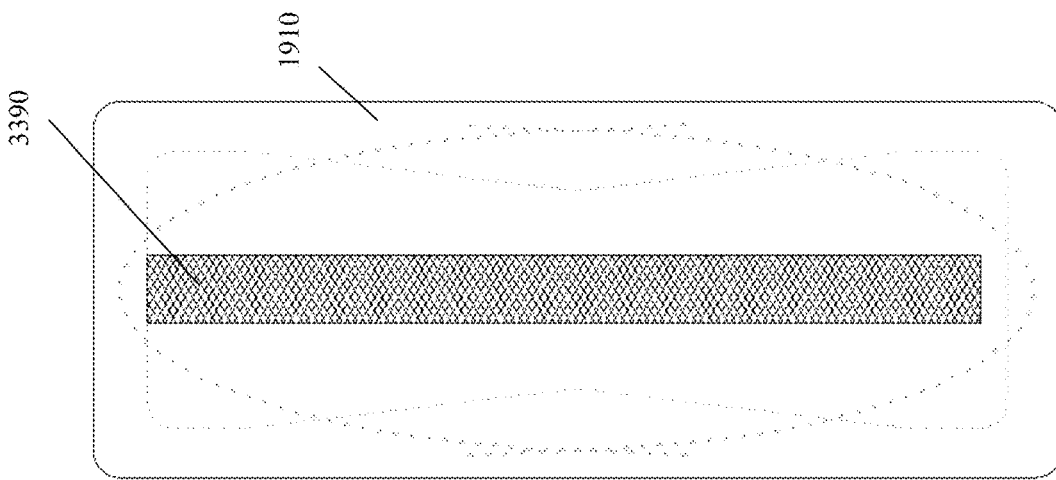
Figure 33A:
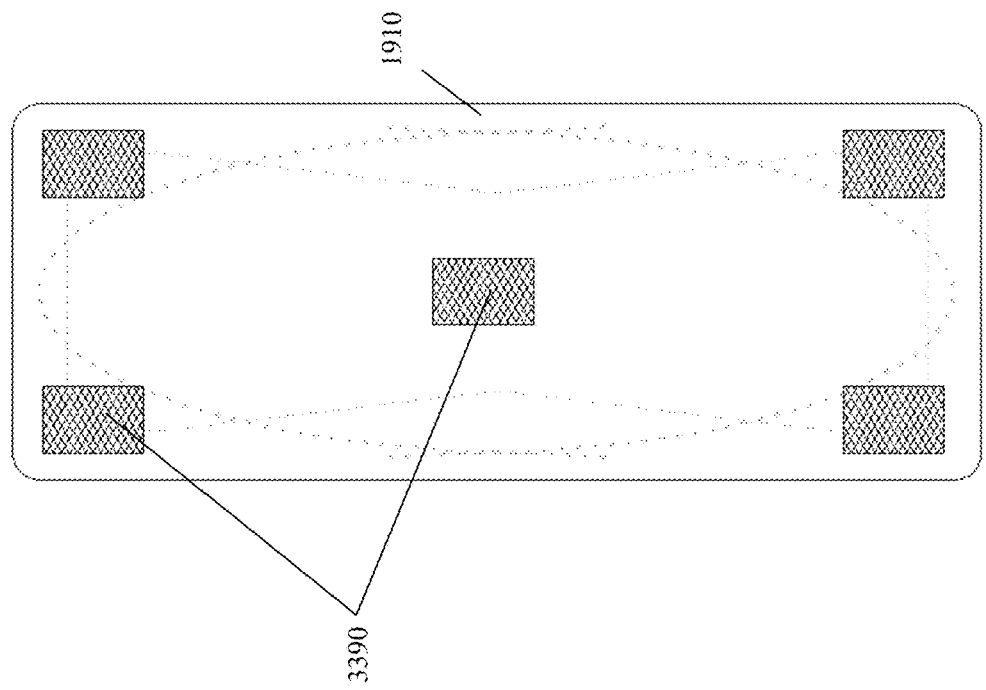
Figure 34A:
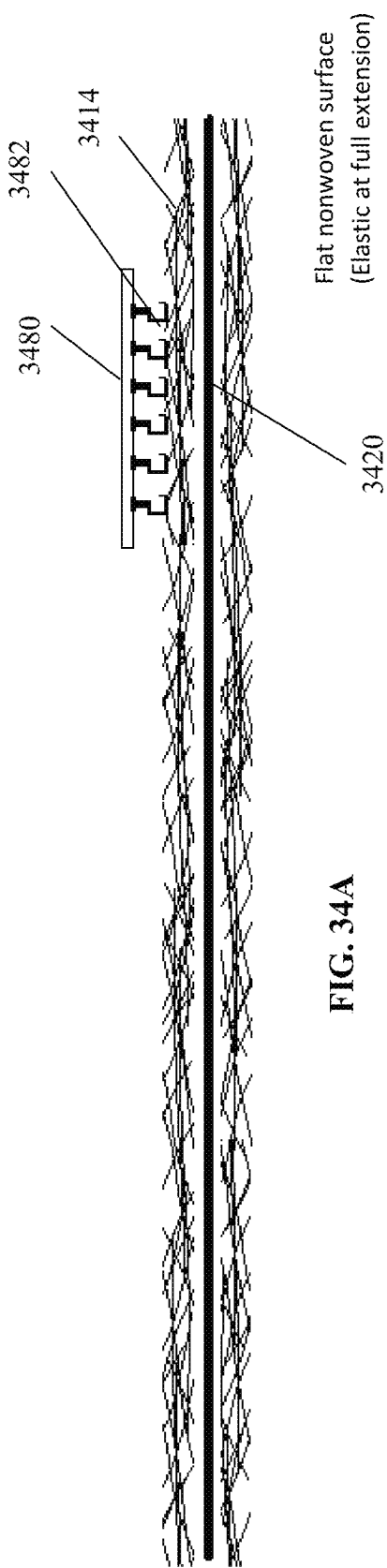
FIG. 34A is a detail cross sectional view of an elasticated fastening or securing means region for an outer shell and core insert combination, at generally full extension.
Figure 34B:
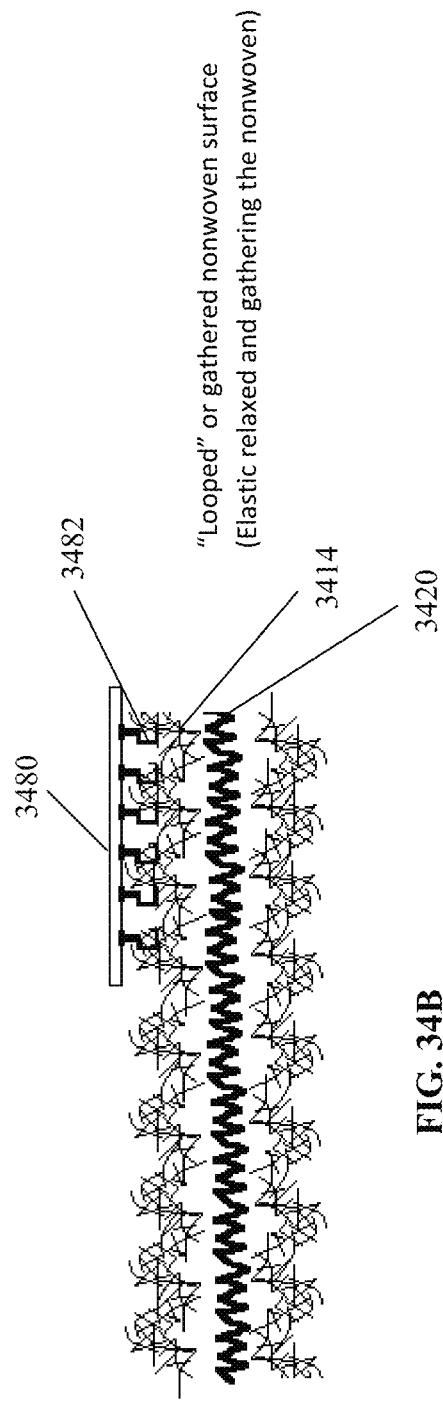
FIG. 34B is a detail cross sectional view of the elasticated region in FIG. 33A at relaxed state.

In various embodiments, the means for detachably securing the absorbent core insert with the outer shell may be achieved by hook and loop systems. The hook or loop part of any individual hook and loop pair may be provided on either the outer shell or the back sheet of the absorbent core insert. Each of FIGS. 33A-33C shows preferred location(s) of hook patches 3390 on the core insert 1910. It should be apparent, however, that the depicted hook patches 3390 may be mounted on corresponding locations on the outer shell. Moreover, the loop part of any such pair may be provided by the surface of a nonwoven layer on the outer shell or of the absorbent core insert. In the latter case, the hook regions on the outer shell need only be provided once (as oppose to each core insert), thereby possibly reducing material cost. FIGS. 34A and 34B illustrate the effective use of elastics 3420 in the absorbent core insert or in the outer shell to enhance the performance of a nonwoven layer 3414 as a source of the loop element. A hook attachment 3480 (e.g., a patch on the backsheet of the core insert) is shown above a region of an elastic composite of two nonwoven layers 3414, 3418 and an elastic strand 3420 disposed in between the nonwovens. If the elastic composite is in a region of the core layer, only one nonwoven layer will be shown. FIG. 34A shows the region near fully extended. Hook elements 3482 of the hook attachment 3480 are shown disengaged from the nonwoven layer 3414. When the elasticized region is relaxed, as in FIG. 34B, the gathering of the nonwoven material projects and presents or pronounces fibers or filaments that function as loop elements. In this state, the nonwoven more readily and more fully engages the hook elements 3482.

The hook element or hook fastener may also be formed on the desired nonwoven surface by an ultrasonic bonding method (ultrasonic bonded formed hooks. (See e.g., U.S. Pat. No. 8,784,722 "Method and Apparatus for Producing Hook Fasteners" for a description of a suitable method). By this method, hooks may be formed directly on a substrate, preferably on a PE backsheet layer. The hooks may be placed anywhere appropriate for locating the core insert-outer shell fasteners and in any configuration.

A hook fastener may also be utilized to add stiffness to a particular area (of the core insert) due to its inherent stiffness. It may also contribute stiffness by virtue of it joining members and immobilizing the affected components. For example, a fastening area in the target zone could add stiffness if needed. Conversely, proper arrangement of the fasteners can encourage folding. For example, in the crotch area, if a v-type fold is advantageous, that configuration may be encouraged by placing two strips of hook fasteners on either side of the longitudinal center line. The composite can then fold more easily along the machine direction (MD) centerline. In addition, if the outer shell is elasticated (e.g., as provided in earlier chassis configurations in FIGS. 1-11) in the cross direction, then folding may be enhanced.

In further embodiments, a secondary disposable nonwoven layer may be provided on the shell (on the core insert landing) and beneath the core insert. Such an additional nonwoven layer may be of a low basis weight, meltblown nonwoven. This additional secondary layer is intended to be separate from the core insert but is also detachable from the inside surface of the outer shell for disposal. To make detachable (and disposable), the additional secondary layer may be applied with a peelable, pressure sensitive adhesive that is applied over some or all of the inside surface or landing area on the outer shell. Alternatively, the additional secondary layer may be applied with adhesive or other adherence means for detachably attaching to the inside surface of the outer shell. Accordingly, multiple secondary layers may be used with the one outer shell and multiple core inserts may be used with one secondary layer. Placed underneath the core insert, this additional disposable layer serves to catch and\or absorb waste spillage and soiling that may otherwise reach the outer shell. This minimizes cleaning or soiling of the outer shell, thereby prolonging or promoting its further use. In further embodiments, the disposable absorbent article is equipped with multiple detachable layers.

Figure 35:
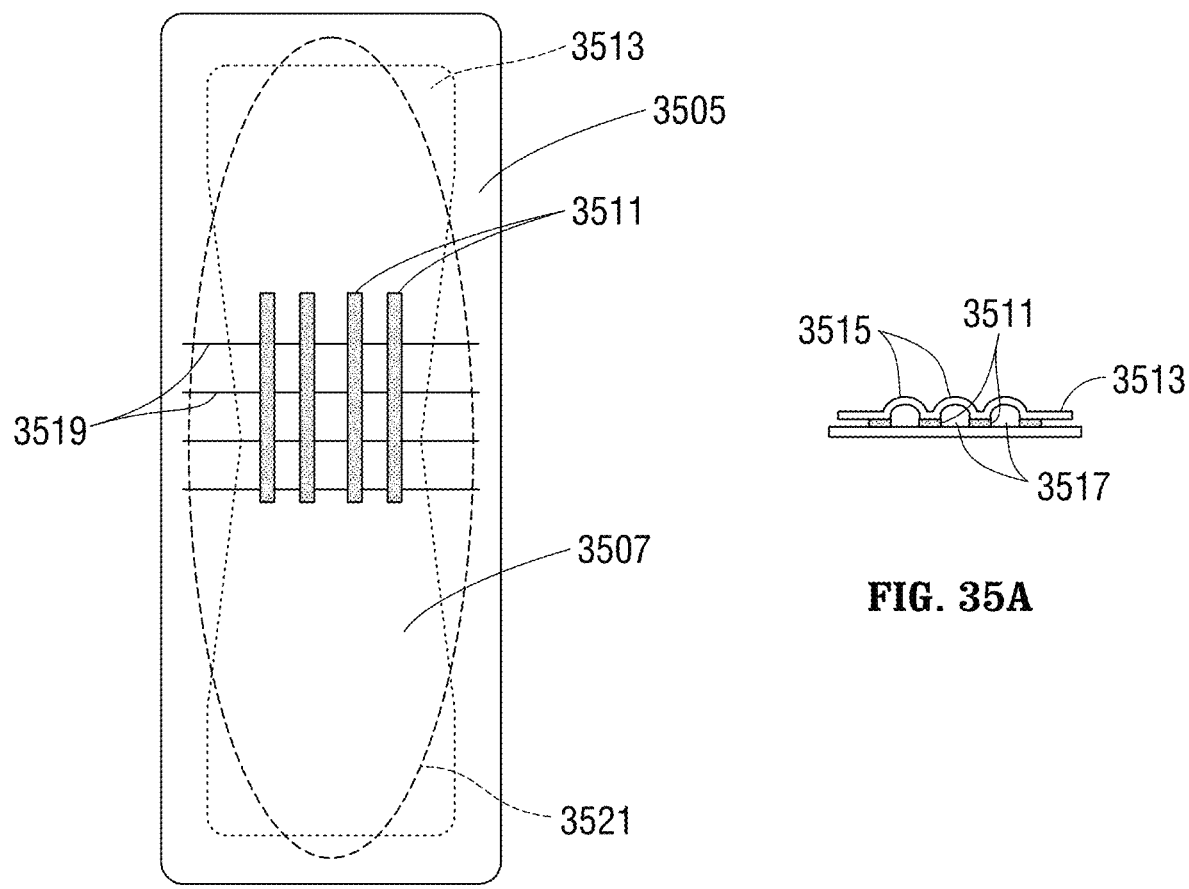
FIG. 35 is a plan view showing an outer shell and core insert according to a further embodiment.

Referring to FIG. 35, in a further embodiment, a plurality of spaced apart fastening strips 3511 (oriented in the machine direction) are provided on the inside surface of an outer shell 3505 (in the landing area 3507) detachably engageable with a core insert 3513 (shown only in broken lines in FIG. 35). FIG. 35A provides a lateral (CD-direction) cross-sectional view of a disposable absorbent article having the outer shell 3505 and a detachable core insert 3513 (the core envelope 3513 is shown in simplified form) supported on the inside surface of the outer shell 3505. The fastening strips 3511 are spaced apart and thus, fixes the core insert envelope 3513 at fixed intervals, as shown in FIG. 35A. Such placement of the fastening strips 3511 promotes formation of multiple corrugations 3517 in or beneath the core insert envelope 3513, which also results in corresponding voids spaces 3517 between the core envelope 3513 and outer shell 3505 and in between the fastening strips 3511. In further embodiments, formation of the corrugations are enhanced and assisted by elastication on the chassis of the outer shell 3505 (and sometimes, elastication on the core insert). In the embodiment of FIG. 35, cross-directional elastics 3519 are provided. Elongated in the longitudinal direction, the void spaces provide and act as channels 3517 that contribute to improved air exchange between the absorbent article and the outside environment. This, not only enhances comfort, but also potentially lower relative humidity in the skin microclimate, thereby promoting skin health. Such conditions also promote longevity of the outer shell and increased number of core insert usage with the outer shell.

In further embodiments, the fastening strips extend toward and near the end longitudinal margins of the core insert, so as to ensure extension of the channels to same end margins. In this way, communication between the channel and outside air is enhanced. In other embodiments, the voids spaces or channels extend in the lateral or cross direction.

Figures 36, 36A:
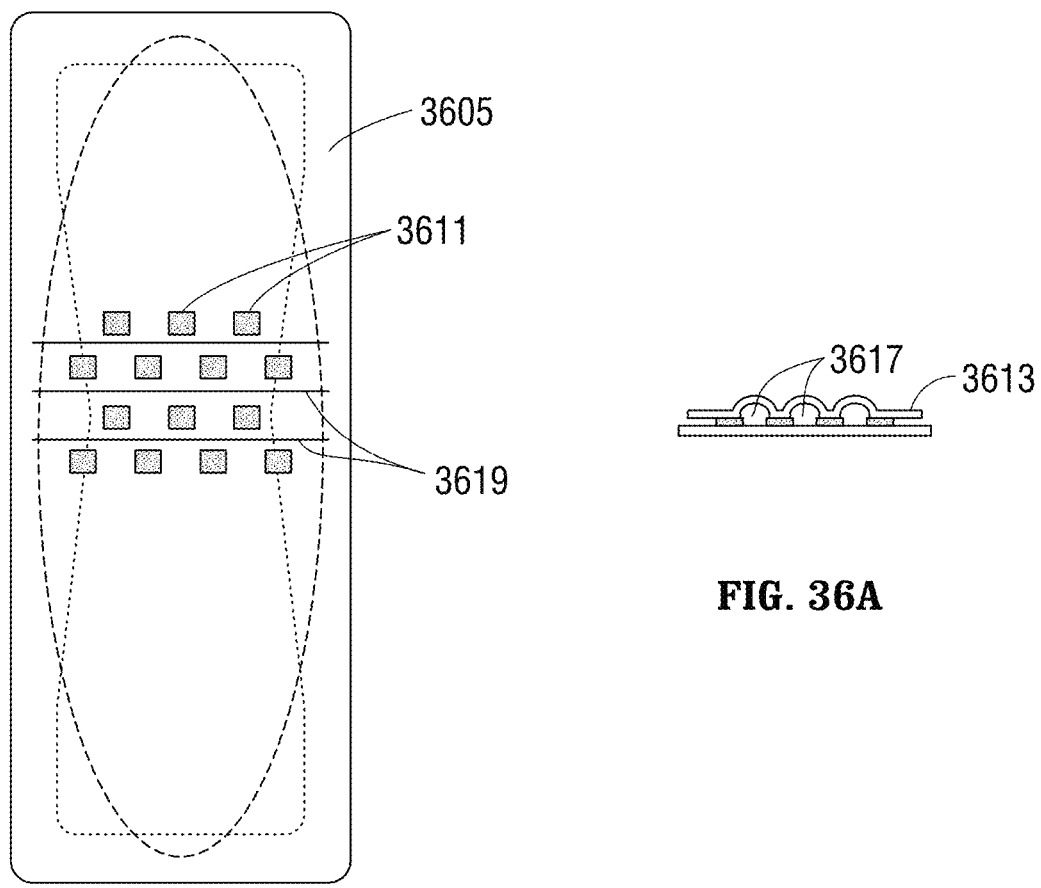
FIG. 36 is a plan view showing an outer shell and core insert according to an alternative embodiment.
FIG. 36A is a cross-sectional view showing the outer shell and core insert in FIG. 36.

FIGS. 36 and 36A illustrates an alternative embodiment utilizing a different arrangement of fasteners to form an alternative configuration of channels, wherein like elements are indicated by like reference numerals. In another respect, FIG. 36 employs a different arrangement of removable\detachable fastening points between the core insert and the outer shell to form the channels 3617. In other words, different types of fasteners may be employed so long as their arrangement provide an arrangement of spaced apart fixed points to create the desired void spaces 3617 (which make the channels 3617). In FIG. 36, the elongated fastening strips are replaced with discrete fastener pads. Each fastening pad 3611 provides more of a fixed point that results in a focused depression (as viewed from above). The result is a pillowy structure that enhances the comfort and feel of the insert.

The employment of cross directional elastics (in the outer shell chassis) in the configurations of FIGS. 35 and 36 provides channels that are more pronounced (not as flat as without elastics) and have relatively greater volume. By concentrating the elastics centrally but extending the channels longitudinally, an advantageous gradient in the channel volume is formed (larger in the elasticated zone and smaller elsewhere). The function and benefit of the air gap still exists since the outer shell is air permeable and air exchange is enhanced. Secondly, the disposable absorbent article is typically most saturated in the crotch area, so placement of elastics and more pronounced channels in the central region is optimal.

The void spaces or channels discussed above may also be provided by an absorbent core insert composed of pockets or aggregate of superabsorbent particles as discussed above. The pocket patterns form void spaces and channels between the pockets, which also provides a pillowy structure as discussed above. Suitable bonding patterns may be found in WO 2015/002934 A2 and WO 2014/145312 A2, each of which is currently assigned to the assignee of the present applications (both of which are hereby incorporated by reference for all purposes and made a part of the present disclosure). Preferred bonding patterns include those provided in FIGS. 15A-15D of WO 2014/145312 A2. It should be noted that the bonding patterns or configuration will be formed on both sides of the core insert. Thus, the side facing the landing of the outer shell will be so configured.

As described above, an air gap between the outer shell and absorbent core insert promote air exchange between the humid interior of the diaper and the outside environment, thereby lowering the overall relative humidity inside the diaper. Such conditions are conducive to drier skin and better skin health.

FIGS. 37 and 37A illustrate an alternative embodiment employing stiffeners to encourage V-folding, wherein like elements are indicated by like reference numerals. In this embodiment, hook fasteners 3711 are employed as both fastener and stiffener. Being of a stiffer material, the hook fasteners double as stiffeners and fastener to configure to a V-fold when worn. See FIG. 37A.

FIG. 38 illustrates embodiments of disposable absorbent articles (A, B, C) according to the present disclosure as worn by a user. The outer shell 3812 is shown in the FIGURE. Embodiments A through C show illustrate the placement of core insert-outer shell retainers 3810 in the form of clips and plugs combinations, at different placement points. The clip may be made of a soft plastic. Embodiments A-C also shows exemplary elastic configurations for the outer shell chassis suitable for use with the insert. One or more retainers may be used. Preferably, the retainers are arranged along a centerline of the outer shell-core insert. Moreover, the retainer clips (on the outer shell) may be mounted on the outside of the outer shell or inside of the outer shell. It also may be fixed permanently or made removable.

Figure 39A:
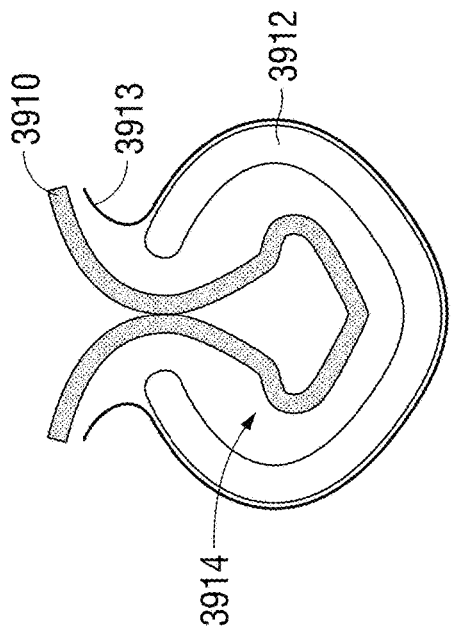
FIGS. 39A-39D are simplified detail illustrations, in cross-sectional elevation view, of a core insert detachably engaged with a retainer clip on an outer shell, according to the present disclosure.
Figure 39B:
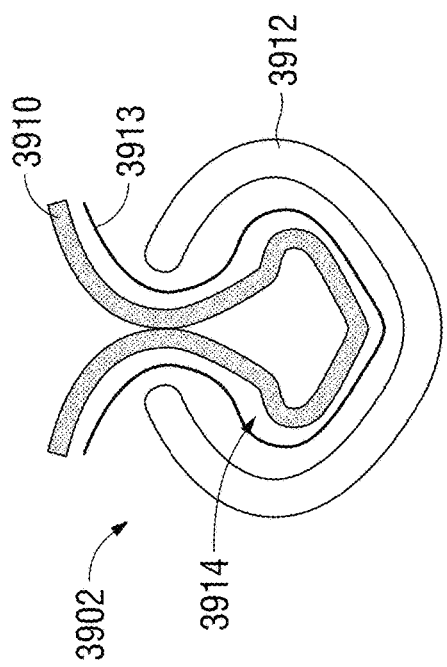
Figure 39C:
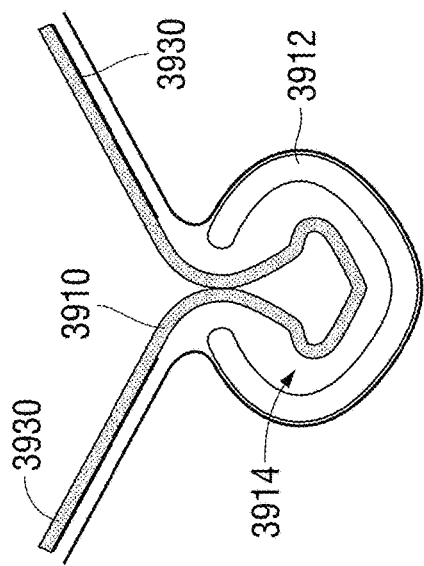
Figure 39D:
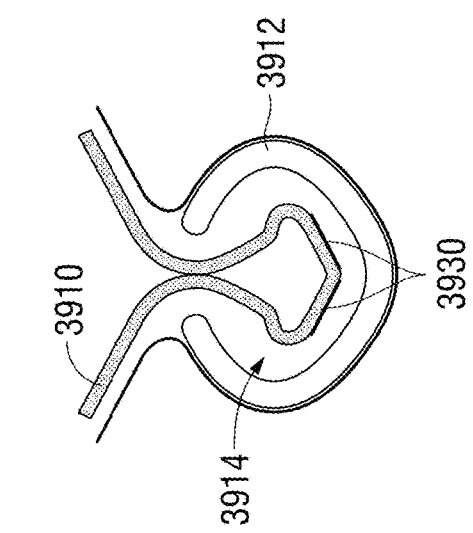

FIGS. 39A-39B show details of alternative core insert-outer shell retainers 3902 for use with disposable absorbent articles, according to the disclosure. As illustrated in FIG. 39A, for example, a protruding bundle 3902 of the core insert (protuberance or plug) is gathered within the narrow jaws of the clip 3912 to retain the core insert 3910 thereto. In FIG. 39B, the retainer or clip 3912 is mounted on the inside of the outer shell 3913. To aid fitting of the insert bundle or plug 3914 in the retainer clip 3912, stiffeners may be employed. In FIG. 39C, two stiffeners 3930 are provided on the point or apex of the bundle or plug. In this arrangement, the stiffeners 3930 help in the actual insertion and retention of the core insert (bundle) in the retainer clip. In FIG. 39D, stiffeners 3930 are provided on a part of the core insert that remains outside of the retainer clip when the core insert is detachably engaged with the outer shell. The stiffeners do not form a part of the core insert bundle or plug. The stiffeners function, however, to add form and direct the fold that defines the bundle or plug, as shown in FIG. 3D.

As described above, disposable absorbent article of the present disclosure provide means for detachably or removably engaged, via fastening, the core insert with outer shell, such that the a new insert may be subsequently fastened with the same outer shell for further use. While engaged, the core insert is retained within the outer shell for use, using the same detachably or removably engaging means. Preferably, that fastening means includes a retaining structure or retainer on the outer shell for engaging, receiving, and retaining the core insert thereto. Furthermore, that fastening means preferably includes a receivable or insertable device or structure on the core insert for receipt and detachable retention in or by the retaining structure. The fastening structures on the outer shell and the core insert, respectively, may however be switched. Any of the combination of fastening structures described herein, including the receptacle (or depression) and protuberance (or plug) and com- bination fasteners and fastening systems like and hoop and loops may be switched, although preferred arrangements are described.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A disposable absorbent article comprising:
    an outer shell;
    a detachable disposable absorbent core insert supported on an inside surface of the outer shell, the core insert being attached to said inside surface and detachable therefrom;
    wherein said inside surface further includes a retaining structure for receiving said core insert, the core insert being attachable with said retaining structure and detachable from said retaining structure;
    wherein the core insert further includes an absorbent material layer disposed between a top layer and a bottom layer; and
    wherein the core insert further includes a stand-up leg cuff forming a circular barrier about said core section, said leg cuff including one or more elastic strands.

2. The absorbent article of claim 1, further comprising a second absorbent core insert attachable to said retaining structure and detachable from said retaining structure.

3. The absorbent article of claim 2, wherein said outer shell includes a landing on said inside surface, each of the first and second core inserts being disposed on said landing upon attachment with said retaining structure.

4. The absorbent article of claim 1, wherein the retaining structure forms part of a hook and loop system provided on the core insert and the outer shell.

5. The absorbent article of claim 1, wherein the core insert further includes one or more elastics disposed along each side of the absorbent material layer and spaced laterally therefrom.

6. The absorbent article of claim 1, wherein the core insert further includes one or more elastics disposed along each side of the absorbent material layer and wherein portions of said elastics contact the absorbent material layer.

7. The absorbent article of claim 1, wherein said outer shell further includes an elasticized leg cuff disposed outwardly from said leg cuff of said core insert.

8. The absorbent article of claim 1, further comprising curved elastics disposed alongside said absorbent material layer.

9. A disposable absorbent core insert for attaching to an outer shell of disposable absorbent article, comprising:
    a top material layer;
    a bottom material layer;

an absorbent core material layer disposed between said top and bottom material layers;

a fastener for attaching the core insert to an inside surface of a reusable outer shell of the absorbent article such that said core insert is detachable therefrom; and a plurality of spaced apart projections on said bottom material layer of said core insert, said projections engageable with the inside surface to provide air channels between said core insert and said inside surface, wherein cross-directional elastics are employed in said air channels.

10. The core insert of claim 9, wherein said air channels extend longitudinally and the cross-directional elastics are disposed centrally to provide air channels of greater volume such that a gradient in a channel volume of said air channels is formed.

11. The core insert of claim 9, wherein said projections are an arrangement of spaced apart fasteners between the core insert and the outer shell, for detachably engaging the core insert with the inside surface of the outer shell, and defining void spaces between said fasteners, said core insert, and the outer shell, the void spaces providing the air channels.

12. The absorbent assembly of claim 11, wherein said void spaces are elongated and extend in the longitudinal direction.

13. A disposable absorbent assembly comprising:
an outer shell;
a disposable absorbent core insert detachably engageable with the outer shell, said core insert including a top material layer, a bottom material layer, and an absorbent core material layer disposed between said top and bottom material layers, said absorbent core material layer having an absorbent composition;
an arrangement of spaced apart fasteners between the core insert and the outer shell, for detachably engaging the core insert with an inside surface of the outer shell, and defining void spaces between said fasteners, said core insert, and said outer shell, the void spaces providing air channels; and
wherein said fasteners and said void spaces are located in a central region of said core insert or outer shell that corresponds to a central crotch region of the absorbent assembly, the fasteners and void spaces being generally centrally located between opposite waist end regions of the outer shell and of the absorbent assembly, and wherein said air channels extend in the lateral direction.

14. The disposable absorbent assembly of claim 13, wherein said fasteners are disposed on said bottom material layer of said core insert and project outwardly to engage the inside surface of the outer shell, said fasteners being spaced apart to define said void spaces between said fasteners, said core insert, and said outer shell, the void spaces providing said air channels extending outward from a central region beneath said core insert.

15. The disposable absorbent assembly of claim 13, wherein said fasteners are space apart projections on said bottom material layer of said core insert, said projections engaging the inside surface of the outer shell to provide said air channels between said core insert and said inside surface.

16. The disposable absorbent assembly of claim 15, wherein said projections include hook fasteners that engage the inside surface of the outer shell.

17. The disposable absorbent assembly of claim 13, wherein said fasteners between said core insert and said outer shell form said air channels.

18. The disposable absorbent assembly of claim 13, wherein said arrangement is an arrangement of fastening strips that promote formation of multiple corrugations in or beneath the core insert and corresponding void spaces between the core insert and outer shell and in between the fastening strips.

19. The disposable absorbent assembly of claim 13, wherein said fasteners extend toward and near end longitudinal margins of the core insert.

20. The disposable absorbent assembly of claim 13, wherein said arrangement is an arrangement of fastening points between the core insert and the outer shell forming said air channels.

21. The disposable absorbent assembly of claim 13, wherein said arrangement is an arrangement of fastening points between the core insert and the outer shell forming said air channels, said fasteners being discrete fastening pads spaced apart on the outer shell.

22. The core insert of claim 9, wherein the core insert includes pockets of absorbent material that form said projections in a pattern in said bottom material layer and said air channels.

23. The core insert of claim 9, wherein said projections are concentrated centrally on said bottom material layer.

24. A disposable absorbent assembly comprising:
an outer shell;
a disposable absorbent core insert detachably engageable with the outer shell, said core insert including a top material layer, a bottom material layer, and an absorbent core material layer disposed between said top and bottom material layers, said absorbent core material layer having an absorbent composition;
an arrangement of spaced apart fasteners between the core insert and the outer shell, for detachably engaging the core insert with an inside surface of the outer shell, and defining void spaces between said fasteners, said core insert, and said outer shell, the void spaces providing air channels;
wherein said fasteners and said void spaces are located in a central region of said core insert or outer shell that corresponds to a central crotch region of the absorbent assembly, the fasteners and void spaces being generally centrally located between opposite waist end regions of the outer shell and of the absorbent assembly; and
wherein cross-directional elastics are employed in said core insert or outer shell and across the fasteners and air channels.

25. The disposable absorbent assembly of claim 24, wherein said air channels extend longitudinally and said cross-directional elastics are disposed centrally to provide said air channels of greater volume such that a gradient in a channel volume of said air channels is formed.

26. The absorbent assembly of claim 24, wherein said cross-directional elastics are concentrated centrally on the outer shell and directed laterally, and the air channels extend longitudinally.

27. A disposable absorbent assembly comprising:
an outer shell;
a disposable absorbent core insert detachably engageable with the outer shell, said core insert including a top material layer, a bottom material layer, and an absorbent core material section disposed between said top and bottom material layers, said absorbent core material section having an absorbent composition;
an arrangement of spaced apart fasteners between the core insert and the outer shell, for detachably engaging the core insert with an inside surface of the outer shell, and defining void spaces between said fasteners, said core insert, and said outer shell, the void spaces providing air channels;

wherein said fasteners and said void spaces are located in a central region of said core insert or outer shell that corresponds to a central crotch region of the absorbent assembly, the fasteners and void spaces being generally centrally located between opposite waist end regions of the outer shell and of the absorbent assembly; and wherein the core insert includes pockets of said absorbent composition in a pattern that form said void spaces and said air channels.

28. A disposable absorbent core insert for attaching to an outer shell of disposable absorbent article, comprising:

a top material layer;

a bottom material layer;

an absorbent core material layer disposed between said top and bottom material layers;

a fastener for attaching the core insert to an inside surface of a reusable outer shell of the absorbent article such that said core insert is detachable therefrom;

wherein said fastener includes a protruding portion on said bottom material layer conformed to detachably engage a receptacle on the outer shell and elastic strands disposed about said protruding portion to partially define said protruding portion.

29. The core insert of claim 28, further comprising a stiffener forming, at least partially, folds that form, at least partially, said protruding portion.

30. A disposable absorbent article comprising:

an outer shell;

a detachable disposable absorbent core insert supported on an inside surface of the outer shell, the core insert being attached to said inside surface and detachable therefrom; and wherein said inside surface further includes a retaining structure for receiving said core insert, the core insert being attachable with said retaining structure and detachable from said retaining structure, wherein said retaining structure includes a receptacle retaining the core insert within said outer shell, the core insert being disengageable from said receptacle and from said outer shell, wherein said receptacle includes a clip defining, at least partially, a shape of said receptacle.

31. The disposable absorbent assembly of claim 30, further comprising folds in the core insert forming, at least partially, a protuberance insertable in said clip in the outer shell to removably attach the clip of said receptacle thereto and removably attach the core insert with the outer shell.

\* \* \* \* \*